(12) United States Patent
Sowards et al.

(10) Patent No.: US 12,419,694 B2
(45) Date of Patent: Sep. 23, 2025

(54) REFERENCE PLANE FOR MEDICAL DEVICE PLACEMENT

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/971,873

(22) Filed: Oct. 24, 2022

(65) Prior Publication Data
US 2023/0126813 A1 Apr. 27, 2023

Related U.S. Application Data

(60) Provisional application No. 63/271,630, filed on Oct. 25, 2021.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/066* (2013.01); *A61B 5/308* (2021.01);
(Continued)

(58) Field of Classification Search
CPC ......... A61B 34/20; A61B 5/308; A61B 5/066; A61B 2034/2061; A61B 2562/0266; G02B 6/02042; G02B 6/02057
See application file for complete search history.

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| CN | 101132730 A | 2/2008 |
| CN | 111265309 A | 6/2020 |

(Continued)

OTHER PUBLICATIONS

PCT/US2023/033471 filed Sep. 22, 2023 International Search Report and Written Opinion dated Dec. 21, 2023.
(Continued)

*Primary Examiner* — Sean A Frith
(74) *Attorney, Agent, or Firm* — Rutan & Tucker LLP

(57) ABSTRACT

A system and method directed to detecting placement of a medical device within a patient body, the system including a medical device including an optical fiber having core fibers. Each of the one or more core fibers can include a plurality of sensors each configured to reflect a light signal having an altered characteristic due to strain experienced by the optical fiber. The system can further include logic configured to determine a 3D shape of the medical device in accordance with the strain of the optical fiber. The logic can be configured to define a reference plane for the 3D shape and render an image of the 3D shape on a display of the system in accordance with the reference plane.

31 Claims, 14 Drawing Sheets

(51) Int. Cl.
*A61B 5/308* (2021.01)
*G02B 6/02* (2006.01)

(52) U.S. Cl.
CPC .. G02B 6/02042 (2013.01); *A61B 2034/2061* (2016.02); *A61B 2562/0266* (2013.01); *G02B 6/02057* (2013.01)

(56) References Cited

U.S. PATENT DOCUMENTS

| | | |
|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,280,786 A | 1/1994 | Wlodarczyk et al. |
| 5,423,321 A | 6/1995 | Fontenot |
| 5,454,807 A | 10/1995 | Lennox et al. |
| 5,460,182 A | 10/1995 | Goodman et al. |
| 5,517,997 A | 5/1996 | Fontenot |
| 5,622,170 A | 4/1997 | Schulz |
| 5,740,808 A | 4/1998 | Panescu et al. |
| 5,841,131 A | 11/1998 | Schroeder et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,245,103 B1 | 6/2001 | Stinson |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,673,214 B1 | 1/2004 | Marchitto et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Kom |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,060,687 B2 | 6/2015 | Yamanaka et al. |
| 9,114,226 B1 | 8/2015 | Lash et al. |
| 9,206,309 B2 | 12/2015 | Appleby et al. |
| 9,360,630 B2 | 6/2016 | Jenner et al. |
| 9,504,392 B2 | 11/2016 | Caron et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,258,240 B1 | 4/2019 | Eberle et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 11,525,670 B2 | 12/2022 | Messerly et al. |
| 2001/0014793 A1 | 8/2001 | Brugger et al. |
| 2002/0198457 A1 | 12/2002 | Tearney et al. |
| 2003/0092995 A1 | 5/2003 | Thompson |
| 2004/0129555 A1 | 7/2004 | Marchitto et al. |
| 2004/0161362 A1 | 8/2004 | Bogert |
| 2004/0242995 A1 | 12/2004 | Maschke |
| 2005/0033264 A1 | 2/2005 | Redinger |
| 2005/0163424 A1 | 7/2005 | Chen |
| 2005/0261598 A1 | 11/2005 | Banet et al. |
| 2005/0278010 A1 | 12/2005 | Richardson |
| 2006/0013523 A1 | 1/2006 | Childlers et al. |
| 2006/0015136 A1 | 1/2006 | Besselink |
| 2006/0036164 A1 | 2/2006 | Wilson et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 | 7/2007 | Larkin et al. |
| 2007/0201793 A1 | 8/2007 | Askins et al. |
| 2007/0287886 A1 | 12/2007 | Saadat |
| 2007/0287934 A1 | 12/2007 | Babaev |
| 2007/0299425 A1 | 12/2007 | Waner et al. |
| 2008/0039715 A1 | 2/2008 | Wilson et al. |
| 2008/0077225 A1 | 3/2008 | Carlin et al. |
| 2008/0082004 A1 | 4/2008 | Banet et al. |
| 2008/0172119 A1 | 7/2008 | Yamasaki et al. |
| 2008/0183128 A1 | 7/2008 | Morriss et al. |
| 2008/0212082 A1 | 9/2008 | Froggatt et al. |
| 2008/0285909 A1 | 11/2008 | Younge et al. |
| 2008/0319290 A1 | 12/2008 | Mao et al. |
| 2009/0054908 A1 | 2/2009 | Zand et al. |
| 2009/0062634 A1 | 3/2009 | Say et al. |
| 2009/0118612 A1 | 5/2009 | Grunwald et al. |
| 2009/0137952 A1 | 5/2009 | Ramamurthy et al. |
| 2009/0234328 A1 | 9/2009 | Cox et al. |
| 2009/0304582 A1 | 12/2009 | Rousso et al. |
| 2009/0314925 A1 | 12/2009 | Van Vorhis et al. |
| 2010/0016729 A1 | 1/2010 | Futrell |
| 2010/0030063 A1 | 2/2010 | Lee et al. |
| 2010/0030132 A1 | 2/2010 | Niezgoda et al. |
| 2010/0063534 A1 | 3/2010 | Kugler et al. |
| 2010/0114115 A1 | 5/2010 | Schlesinger et al. |
| 2010/0286531 A1 | 11/2010 | Ryan et al. |
| 2010/0312095 A1 | 12/2010 | Jenkins et al. |
| 2011/0060229 A1 | 3/2011 | Hulvershorn et al. |
| 2011/0090486 A1 | 4/2011 | Udd |
| 2011/0144481 A1 | 6/2011 | Feer et al. |
| 2011/0166442 A1 | 7/2011 | Sarvazyan |
| 2011/0172591 A1 | 7/2011 | Babaev |
| 2011/0172680 A1 | 7/2011 | Younge et al. |
| 2011/0237958 A1 | 9/2011 | Onimura |
| 2011/0242532 A1 | 10/2011 | McKenna |
| 2011/0245662 A1 | 10/2011 | Eggers et al. |
| 2011/0288405 A1 | 11/2011 | Razavi et al. |
| 2011/0295108 A1 | 12/2011 | Cox et al. |
| 2011/0313280 A1 | 12/2011 | Govari et al. |
| 2012/0046562 A1 | 2/2012 | Powers et al. |

(56) References Cited

U.S. PATENT DOCUMENTS

| | | |
|---|---|---|
| 2012/0065481 A1 | 3/2012 | Hunter et al. |
| 2012/0101413 A1 | 4/2012 | Beetel et al. |
| 2012/0136242 A1 | 5/2012 | Qi et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0283747 A1 | 11/2012 | Popovic |
| 2012/0289783 A1* | 11/2012 | Duindam ............... A61B 5/065 600/118 |
| 2012/0321243 A1 | 12/2012 | Younge et al. |
| 2013/0028554 A1 | 1/2013 | Wong et al. |
| 2013/0072943 A1 | 3/2013 | Parmar |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0317372 A1 | 11/2013 | Eberle et al. |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0124264 A1 | 5/2015 | Ramachandran et al. |
| 2015/0141808 A1 | 5/2015 | Elhawary et al. |
| 2015/0141854 A1 | 5/2015 | Eberle et al. |
| 2015/0164571 A1 | 6/2015 | Saadat |
| 2015/0190221 A1 | 7/2015 | Schaefer et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1 | 11/2015 | Vitullo et al. |
| 2016/0018602 A1 | 1/2016 | Govari et al. |
| 2016/0067449 A1 | 3/2016 | Misener et al. |
| 2016/0102969 A1 | 4/2016 | Verstege et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0213432 A1* | 7/2016 | Flexman ............... A61B 5/065 |
| 2016/0331461 A1 | 11/2016 | Cheatham, III et al. |
| 2016/0349044 A1 | 12/2016 | Marell et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |
| 2017/0151027 A1 | 6/2017 | Walker et al. |
| 2017/0173349 A1 | 6/2017 | Pfleiderer et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290563 A1 | 10/2017 | Cole et al. |
| 2017/0311901 A1 | 11/2017 | Zhao et al. |
| 2017/0319279 A1 | 11/2017 | Fish et al. |
| 2018/0008443 A1 | 1/2018 | Cole et al. |
| 2018/0031493 A1 | 2/2018 | Tojo et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0139392 A1* | 5/2018 | Rauniyar ............... A61B 8/12 |
| 2018/0140170 A1 | 5/2018 | Van Putten et al. |
| 2018/0235709 A1* | 8/2018 | Donhowe ............... G06T 7/33 |
| 2018/0239124 A1 | 8/2018 | Naruse et al. |
| 2018/0240237 A1 | 8/2018 | Donhowe et al. |
| 2018/0250088 A1 | 9/2018 | Brennan et al. |
| 2018/0264227 A1 | 9/2018 | Flexman et al. |
| 2018/0279909 A1* | 10/2018 | Noonan ............... A61B 90/37 |
| 2018/0289390 A1 | 10/2018 | Amorizzo et al. |
| 2018/0289927 A1* | 10/2018 | Messerly ............... G01L 1/242 |
| 2018/0339134 A1 | 11/2018 | Leo |
| 2018/0360545 A1 | 12/2018 | Cole et al. |
| 2019/0059743 A1 | 2/2019 | Ramachandran et al. |
| 2019/0060003 A1 | 2/2019 | Tuason |
| 2019/0110844 A1 | 4/2019 | Misener et al. |
| 2019/0231272 A1 | 8/2019 | Yamaji |
| 2019/0237902 A1 | 8/2019 | Thompson et al. |
| 2019/0247132 A1 | 8/2019 | Harks et al. |
| 2019/0307331 A1 | 10/2019 | Saadat et al. |
| 2019/0321110 A1 | 10/2019 | Grunwald et al. |
| 2019/0343424 A1 | 11/2019 | Blumenkranz et al. |
| 2019/0343702 A1 | 11/2019 | Smith |
| 2019/0357875 A1 | 11/2019 | Qi et al. |
| 2019/0365199 A1 | 12/2019 | Zhao et al. |
| 2019/0374130 A1 | 12/2019 | Bydlon et al. |
| 2020/0000526 A1 | 1/2020 | Zhao |
| 2020/0030575 A1 | 1/2020 | Bogusky et al. |
| 2020/0046434 A1 | 2/2020 | Graetzel et al. |
| 2020/0054399 A1 | 2/2020 | Duindam et al. |
| 2020/0121482 A1 | 4/2020 | Spector et al. |
| 2020/0188036 A1 | 6/2020 | Ding et al. |
| 2020/0297442 A1 | 9/2020 | Adebar et al. |
| 2020/0305983 A1 | 10/2020 | Yampolsky et al. |
| 2020/0315770 A1 | 10/2020 | Dupont et al. |
| 2020/0394789 A1 | 12/2020 | Freund et al. |
| 2021/0015470 A1 | 1/2021 | Prisco et al. |
| 2021/0023341 A1 | 1/2021 | Decheek et al. |
| 2021/0045814 A1 | 2/2021 | Thompson et al. |
| 2021/0068911 A1 | 3/2021 | Walker et al. |
| 2021/0100627 A1 | 4/2021 | Soper et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0298680 A1 | 9/2021 | Sowards et al. |
| 2021/0330399 A1 | 10/2021 | Netravali et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0011192 A1 | 1/2022 | Misener et al. |
| 2022/0034733 A1 | 2/2022 | Misener et al. |
| 2022/0079683 A1 | 3/2022 | Bydlon et al. |
| 2022/0096796 A1 | 3/2022 | McLaughlin et al. |
| 2022/0110508 A1 | 4/2022 | Van Roosbroeck et al. |
| 2022/0110695 A1 | 4/2022 | Sowards et al. |
| 2022/0151568 A1 | 5/2022 | Yao et al. |
| 2022/0152349 A1 | 5/2022 | Sowards et al. |
| 2022/0160209 A1 | 5/2022 | Sowards et al. |
| 2022/0172354 A1 | 6/2022 | Misener et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0243715 A1 | 8/2023 | Misener et al. |
| 2023/0248444 A1 | 8/2023 | Misener et al. |
| 2023/0251150 A1 | 8/2023 | Misener et al. |
| 2023/0337985 A1 | 10/2023 | Sowards et al. |
| 2023/0346479 A1 | 11/2023 | Muller et al. |
| 2023/0414112 A1 | 12/2023 | Misener et al. |
| 2024/0000515 A1 | 1/2024 | Misener et al. |
| 2024/0050708 A1 | 2/2024 | Misener |
| 2024/0099659 A1 | 3/2024 | Sowards et al. |
| 2024/0108856 A1 | 4/2024 | Messerly |
| 2024/0216077 A1 | 7/2024 | Thompson et al. |
| 2024/0335237 A1 | 10/2024 | Sowards et al. |
| 2024/0353275 A1 | 10/2024 | Misener et al. |
| 2024/0383133 A1 | 11/2024 | Bydlon et al. |
| 2024/0390644 A1 | 11/2024 | Mclaughlin et al. |
| 2025/0020453 A1 | 1/2025 | Thompson et al. |
| 2025/0060266 A1 | 2/2025 | Messerly |

(56) References Cited

U.S. PATENT DOCUMENTS

| | | |
|---|---|---|
| 2025/0186135 A1 | 6/2025 | McLaughlin et al. |
| 2025/0224304 A1 | 7/2025 | Misener et al. |

FOREIGN PATENT DOCUMENTS

| | | |
|---|---|---|
| CN | 113080937 A | 7/2021 |
| DE | 102016109601 A1 | 11/2017 |
| EP | 2240111 A2 | 10/2010 |
| EP | 2907445 A1 | 8/2015 |
| EP | 3545849 A1 | 10/2019 |
| EP | 3705020 A1 | 9/2020 |
| JP | 7366562 B2 | 10/2023 |
| KR | 20190098512 A | 8/2019 |
| WO | 99/64099 A1 | 12/1999 |
| WO | 2006113394 A2 | 10/2006 |
| WO | 2006122001 A2 | 11/2006 |
| WO | 2007002323 A2 | 1/2007 |
| WO | 2009/155325 A2 | 12/2009 |
| WO | 2011121516 A2 | 10/2011 |
| WO | 2011141830 A1 | 11/2011 |
| WO | 2011150376 A1 | 12/2011 |
| WO | 2012064769 A2 | 5/2012 |
| WO | 2015044930 A1 | 4/2015 |
| WO | 2015074045 A2 | 5/2015 |
| WO | 2016038492 A1 | 3/2016 |
| WO | 2016/061431 A1 | 4/2016 |
| WO | 2016051302 A1 | 4/2016 |
| WO | 2016149819 A1 | 9/2016 |
| WO | 2018/096491 A1 | 5/2018 |
| WO | 2019037071 A1 | 2/2019 |
| WO | 2019/046769 A1 | 3/2019 |
| WO | 2019070423 A1 | 4/2019 |
| WO | 2019230713 A1 | 12/2019 |
| WO | 2020182997 A1 | 9/2020 |
| WO | 2021030092 A1 | 2/2021 |
| WO | 2021108688 A1 | 6/2021 |
| WO | 2021108697 A1 | 6/2021 |
| WO | 2021138096 A1 | 7/2021 |
| WO | 2021216089 A1 | 10/2021 |
| WO | 2022/031613 A1 | 2/2022 |
| WO | 2022/081723 A1 | 4/2022 |
| WO | 2022150411 A1 | 7/2022 |
| WO | 2022/164902 A1 | 8/2022 |
| WO | 2022245987 A1 | 11/2022 |
| WO | 2023043954 A1 | 3/2023 |
| WO | 2023049443 A1 | 3/2023 |
| WO | 2023055810 A1 | 4/2023 |
| WO | 2023076143 A1 | 5/2023 |
| WO | 2023211752 A1 | 11/2023 |
| WO | 2024006384 A1 | 1/2024 |
| WO | 2024006441 A1 | 1/2024 |
| WO | 2024064334 A1 | 3/2024 |
| WO | 2024215665 A1 | 10/2024 |

OTHER PUBLICATIONS

U.S. Appl. No. 17/484,960, filed Sep. 24, 2021 Notice of Allowance dated Apr. 12, 2024.
U.S. Appl. No. 17/500,678, filed Oct. 13, 2021 Non-Final Office Action dated Jan. 19, 2024.
U.S. Appl. No. 18/079,653, filed Dec. 12, 2022 Non-Final Office Action dated Feb. 6, 2024.
U.S. Appl. No. 18/135,337, filed Apr. 17, 2023 Notice of Allowance dated Mar. 8, 2024.
EP 20853352.1 filed Mar. 7, 2022 Extended European Search Report dated Jul. 27, 2023.
PCT/US2021/052046 filed Sep. 24, 2021 International Search Report and Written Opinion dated Jan. 11, 2022.
PCT/US2023/019239 filed Apr. 20, 2023 International Search Report and Written Opinion dated Jul. 20, 2023.
PCT/US2023/026487 filed Jun. 28, 2023 International Search Report and Written Opinion dated Sep. 6, 2023.
U.S. Appl. No. 16/984,104, filed Aug. 3, 2020 Final Office Action dated Sep. 21, 2023.
U.S. Appl. No. 16/984,104, filed Aug. 3, 2020 Non-Final Office Action dated Jun. 22, 2023.
U.S. Appl. No. 17/105,310, filed Nov. 25, 2020 Notice of Allowance dated Aug. 2, 2023.
U.S. Appl. No. 17/357,186, filed Jun. 24, 2021 Non Final Office Action dated May 30, 2023.
U.S. Appl. No. 17/357,186, filed Jun. 24, 2021 Notice of Allowance dated Aug. 23, 2023.
U.S. Appl. No. 17/484,960, filed Sep. 24, 2021 Non-Final Office Action dated Oct. 5, 2023.
U.S. Appl. No. 17/500,678, filed Oct. 13, 2021 Final Office Action dated Sep. 21, 2023.
Fiber Optic RealShape (FORS) technology—research. Philips. (Oct. 18, 2018). Retrieved Feb. 28, 2023, from https://www.philips.com/a-w/research/research-programs/fors.html (Year: 2018).
Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
PCT/US2022/047538 filed Oct. 24, 2022 International Search Report and Written Opinion dated Jan. 26, 2023.
U.S. Appl. No. 15/947,267, filed Apr. 6, 2018 Examiner's Answer dated Nov. 28, 2022.
U.S. Appl. No. 16/984,104, filed Aug. 3, 2020 Restriction Requirement dated Mar. 13, 2023.
U.S. Appl. No. 17/105,310, filed Nov. 25, 2020 Non-Final Office Action dated Feb. 22, 2023.
U.S. Appl. No. 17/357,186, filed Jun. 24, 2021 Restriction Requirement dated Mar. 7, 2023.
U.S. Appl. No. 17/357,561, filed Jun. 24, 2021 Notice of Allowance dated Dec. 9, 2022.
U.S. Appl. No. 17/392,002, filed Aug. 2, 2021, Corrected Notice of Allowability dated Feb. 23, 2023.
U.S. Appl. No. 17/392,002, filed Aug. 2, 2021, Notice of Allowance dated Jan. 19, 2023.
U.S. Appl. No. 17/500,678, filed Oct. 13, 2021 Non-Final Office Action dated Mar. 15, 2023.
Dziuda L et al: "Monitoring Respiration and Cardiac Activity Using Fiber Bragg Grating-Based Sensor", IEEE Transactions on Biomedical Engineering vol. 59, No. 7, Jul. 2012 pp. 1934-1942.
Dziuda L. et al: "Fiber-optic sensor for monitoring respiration and cardiac activity", 2011 IEEE Sensors Proceedings : Limerick, Ireland, Oct. 2011 pp. 413-416.
EP 20893677.3 filed Jun. 22, 2022 Extended European Search Report dated Oct. 13, 2023.
EP 20894633.5 filed Jun. 22, 2022 Extended European Search Report dated Oct. 16, 2023.
PCT/US2023/026581 filed Jun. 29, 2023 International Search Report and Written Opinion dated Oct. 27, 2023.
U.S. Appl. No. 16/984,104, filed Aug. 3, 2020 Notice of Allowance dated Nov. 21, 2023.
U.S. Appl. No. 17/500,678, filed Oct. 13, 2021 Advisory Action dated Dec. 7, 2023.
U.S. Appl. No. 18/135,337, filed Apr. 17, 2023 Non-Final Office Action dated Dec. 22, 2023.
U.S. Appl. No. 17/569,350, filed Jan. 5, 2022 Non-Final Office Action dated Jan. 8, 2024.
PCT/US2018/026493 filed Apr. 6, 2018 International Search Report and Written Opinion dated Jun. 22, 2018.
PCT/US2020/044801 filed Aug. 3, 2020 International Search Report and Written Opinion dated Oct. 26, 2020.
PCT/US2020/062396 filed Nov. 25, 2020 International Preliminary Report on Patentability dated Jan. 29, 2021.
PCT/US2020/062396 filed Nov. 25, 2020 International Search Report and Written Opinion dated Mar. 2, 2021.

(56) References Cited

OTHER PUBLICATIONS

PCT/US2020/062407 filed Nov. 25, 2020 International Preliminary Report on Patentability dated Jan. 25, 2021.
PCT/US2020/062407 filed Nov. 25, 2020 International Search Report and Written Opinion dated Mar. 11, 2021.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
PCT/US2021/054802 filed Oct. 13, 2021 International Search Report and Written Opinion dated Feb. 2, 2022.
PCT/US2022/011347 filed Jan. 5, 2022 International Search Report and Written Opinion dated May 3, 2022.
PCT/US2022/013897 filed Jan. 26, 2022 International Search Report and Written Opinion dated May 11, 2022.
PCT/US2022/029894 filed May 18, 2022, International Search Report and Written Opinion dated Sep. 1, 2022.
U.S. Appl. No. 15/947,267, filed Apr. 6, 2018 Final Office Action dated Apr. 22, 2022.
U.S. Appl. No. 17/105,259, filed Nov. 25, 2020, Notice of Allowance dated Jul. 20, 2022.
U.S. Appl. No. 17/357,561, filed Jun. 24, 2021 Non-Final Office Action dated Aug. 11, 2022.
U.S. Appl. No. 17/371,993, filed Jul. 9, 2021 Non-Final Office Action dated Jul. 12, 2022.
U.S. Appl. No. 17/371,993, filed Jul. 9, 2021 Notice of Allowance dated Nov. 3, 2022.
U.S. Appl. No. 17/392,002, filed Aug. 2, 2021, Non-Final Office Action dated Sep. 12, 2022.
U.S. Appl. No. 15/947,267, filed Apr. 6, 2018 Final Office Action dated Jun. 30, 2021.
U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
Mayoral et al. Fiber Optic Sensors for Vital Signs Monitoring. A Review of Its Practicality in the Health Field. Biosensors (Basel). Feb. 23, 2021;11(2):58. doi: 10.3390/bios11020058.
U.S. Appl. No. 15/947,267, filed Apr. 6, 2018 Notice of Allowance dated Jul. 16, 2024.
U.S. Appl. No. 17/500,678, filed Oct. 13, 2021 Final Office Action dated Aug. 27, 2024.
U.S. Appl. No. 17/569,350, filed Jan. 5, 2022 Advisory Action dated Jul. 12, 2024.
U.S. Appl. No. 17/569,350, filed Jan. 5, 2022 Final Office Action dated Apr. 23, 2024.
U.S. Appl. No. 17/728,802, filed Apr. 25, 2022 Non-Final Office Action dated Aug. 28, 2024.
U.S. Appl. No. 17/747,903, filed May 18, 2022 Non-Final Office Action dated Aug. 15, 2024.
U.S. Appl. No. 17/747,903, filed May 18, 2022 Restriction Requirement dated May 28, 2024.
U.S. Appl. No. 17/955,019, filed Sep. 28, 2022 Restriction Requirement dated Jun. 6, 2024.
U.S. Appl. No. 18/079,653, filed Dec. 12, 2022 Notice of Allowance dated Jun. 4, 2024.
U.S. Appl. No. 18/132,231, filed Apr. 7, 2023 Non-Final Office Action dated Jul. 12, 2024.
U.S. Appl. No. 18/132,623, filed Apr. 10, 2023, Non-Final Office Action dated May 3, 2024.
U.S. Appl. No. 18/538,111, filed Dec. 13, 2023 Non-Final Office Action dated Aug. 9, 2024.
U.S. Appl. No. 17/569,350, filed Jan. 5, 2022 Non-Final Office Action dated Aug. 12, 2024.
U.S. Appl. No. 17/500,678, filed Oct. 13, 2021 Advisory Action dated Nov. 6, 2024.
U.S. Appl. No. 17/569,350, filed Jan. 5, 2022 Notice of Allowance dated Nov. 7, 2024.
U.S. Appl. No. 17/585,219, filed Jan. 26, 2022 Restriction Requirement dated Dec. 2, 2024.
U.S. Appl. No. 17/852,138, filed Jun. 28, 2022 Non-Final Office Action dated Sep. 18, 2024.
U.S. Appl. No. 17/853,590, filed Jun. 29, 2022 Non-Final Office Action dated Oct. 17, 2024.
U.S. Appl. No. 17/955,019, filed Sep. 28, 2022 Non-Final Office Action dated Sep. 27, 2024.
U.S. Appl. No. 18/132,623, filed Apr. 10, 2023, Final Office Action dated Sep. 6, 2024.
U.S. Appl. No. 18/132,623, filed Apr. 10, 2023, Notice of Allowance dated Nov. 19, 2024.
U.S. Appl. No. 18/607,144, filed Mar. 15, 2024 Non-Final Office Action dated Sep. 24, 2024.
P.J. de Feyter, P. Kay, C. Disco, P.W. Serruys, "Reference chart derived from post-stent-implantation intravascular ultrasound predictors of 6-month expected restenosis on quantitative coronary angiography." Circulation. vol. 100, No. 17 (Year: 1999).
PCT/US2023/026581 filed Jun. 29, 2023 International Preliminary Report on Patentability dated Dec. 18, 2024.
U.S. Appl. No. 17/500,678, filed Oct. 13, 2021 Non-Final Office Action dated Dec. 4, 2024.
U.S. Appl. No. 17/585,219, filed Jan. 26, 2022 Non-Final Office Action dated Feb. 27, 2025.
U.S. Appl. No. 17/728,802, filed Apr. 25, 2022 Advisory Action dated Apr. 4, 2025.
U.S. Appl. No. 17/728,802, filed Apr. 25, 2022 Final Office Action dated Jan. 17, 2025.
U.S. Appl. No. 17/747,903, filed May 18, 2022 Advisory Action dated Apr. 22, 2025.
U.S. Appl. No. 17/747,903, filed May 18, 2022 Final Office Action dated Jan. 27, 2025.
U.S. Appl. No. 17/852,138, filed Jun. 28, 2022 Notice of Allowance dated Feb. 12, 2025.
U.S. Appl. No. 17/853,590, filed Jun. 29, 2022 Notice of Allowance dated Mar. 5, 2025.
U.S. Appl. No. 17/952,645, filed Sep. 26, 2022 Non-Final Office Action dated Feb. 28, 2025.
U.S. Appl. No. 17/955,019, filed Sep. 28, 2022 Advisory Action dated Apr. 16, 2025.
U.S. Appl. No. 17/955,019, filed Sep. 28, 2022 Final Office Action dated Feb. 4, 2025.
U.S. Appl. No. 18/132,231, filed Apr. 7, 2023 Final Office Action dated Jan. 31, 2025.
U.S. Appl. No. 18/132,231, filed Apr. 7, 2023 Notice of Allowance dated Apr. 10, 2025.
U.S. Appl. No. 18/383,809, filed Oct. 25, 2023 Non-Final Office Action dated Dec. 16, 2024.
U.S. Appl. No. 18/538,111, filed Dec. 13, 2023 Final Office Action dated Feb. 4, 2025.
U.S. Appl. No. 18/538,111, filed Dec. 13, 2023 Notice of Allowance dated Apr. 23, 2025.
U.S. Appl. No. 18/607,144, filed Mar. 15, 2024 Final Office Action dated Feb. 19, 2025.
Ogawa, K.; Koyama, S.; Ishizawa, H.; Fujiwara, S.; Fujimoto, K. Simultaneous Measurement of Heart Sound, PulseWave and Respiration with Single Fiber Bragg Grating Sensor. In Proceedings of the 2018 IEEE International Symposium on Medical Measurements and Applications (MeMeA), Rome, Italy, Jun. 11-13, 2018.
U.S. Appl. No. 17/500,678, filed Oct. 13, 2021 Final Office Action dated Jun. 11, 2025.
U.S. Appl. No. 17/585,219, filed Jan. 26, 2022 Notice of Allowance dated Jun. 17, 2025.
U.S. Appl. No. 17/728,802, filed Apr. 25, 2022 Non-Final Office Action dated May 19, 2025.
U.S. Appl. No. 17/952,645, filed Sep. 26, 2022 Final Office Action dated Jul. 14, 2025.

(56) References Cited

OTHER PUBLICATIONS

U.S. Appl. No. 18/132,891, filed Apr. 10, 2023 Restriction Requirement dated Jun. 2, 2025.
U.S. Appl. No. 18/383,809, filed Oct. 25, 2023 Notice of Allowance dated Apr. 30, 2025.

* cited by examiner

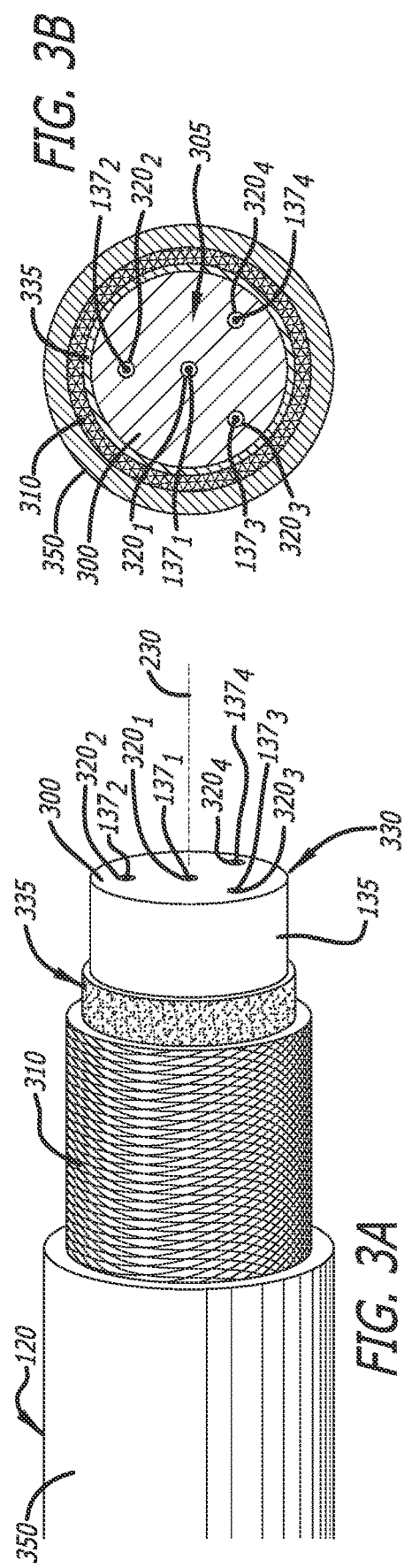
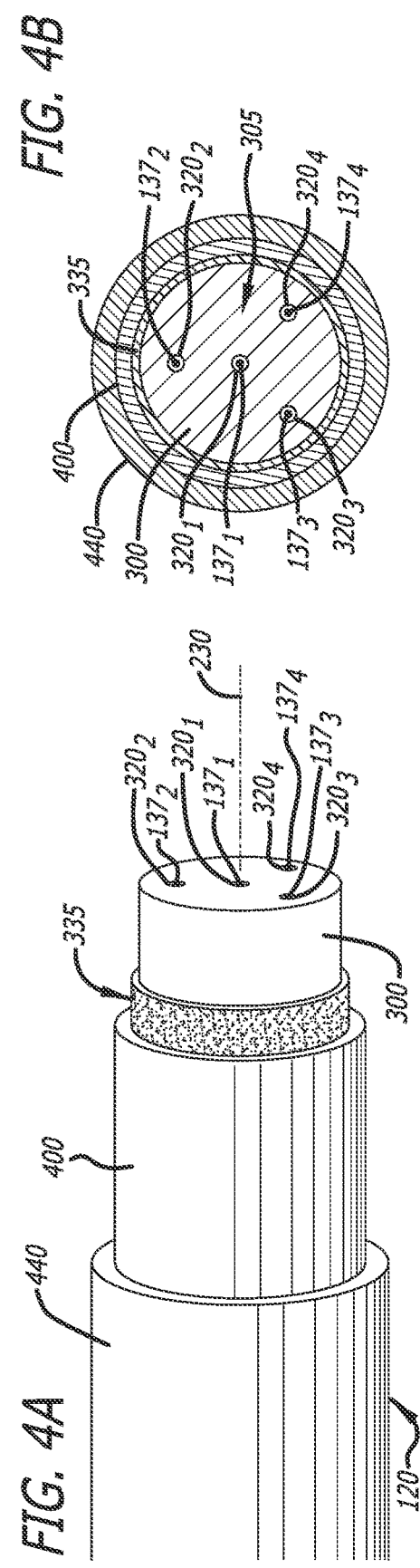

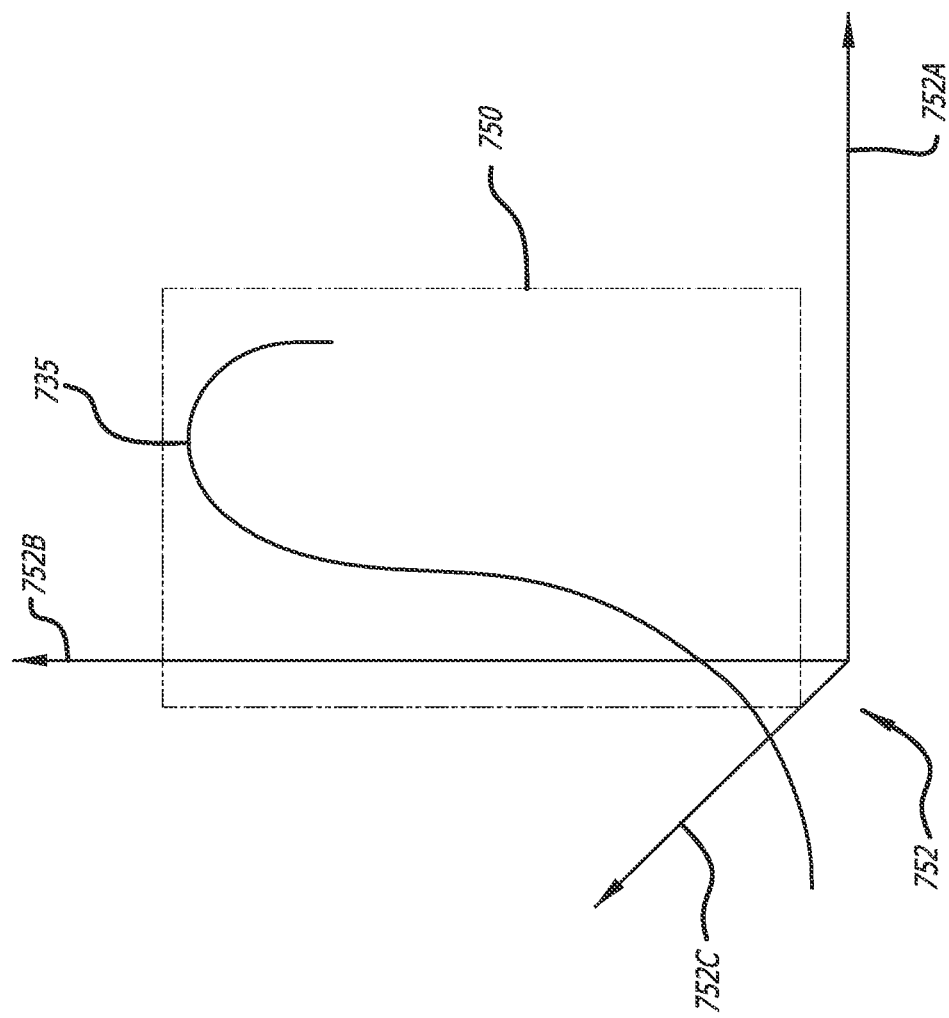

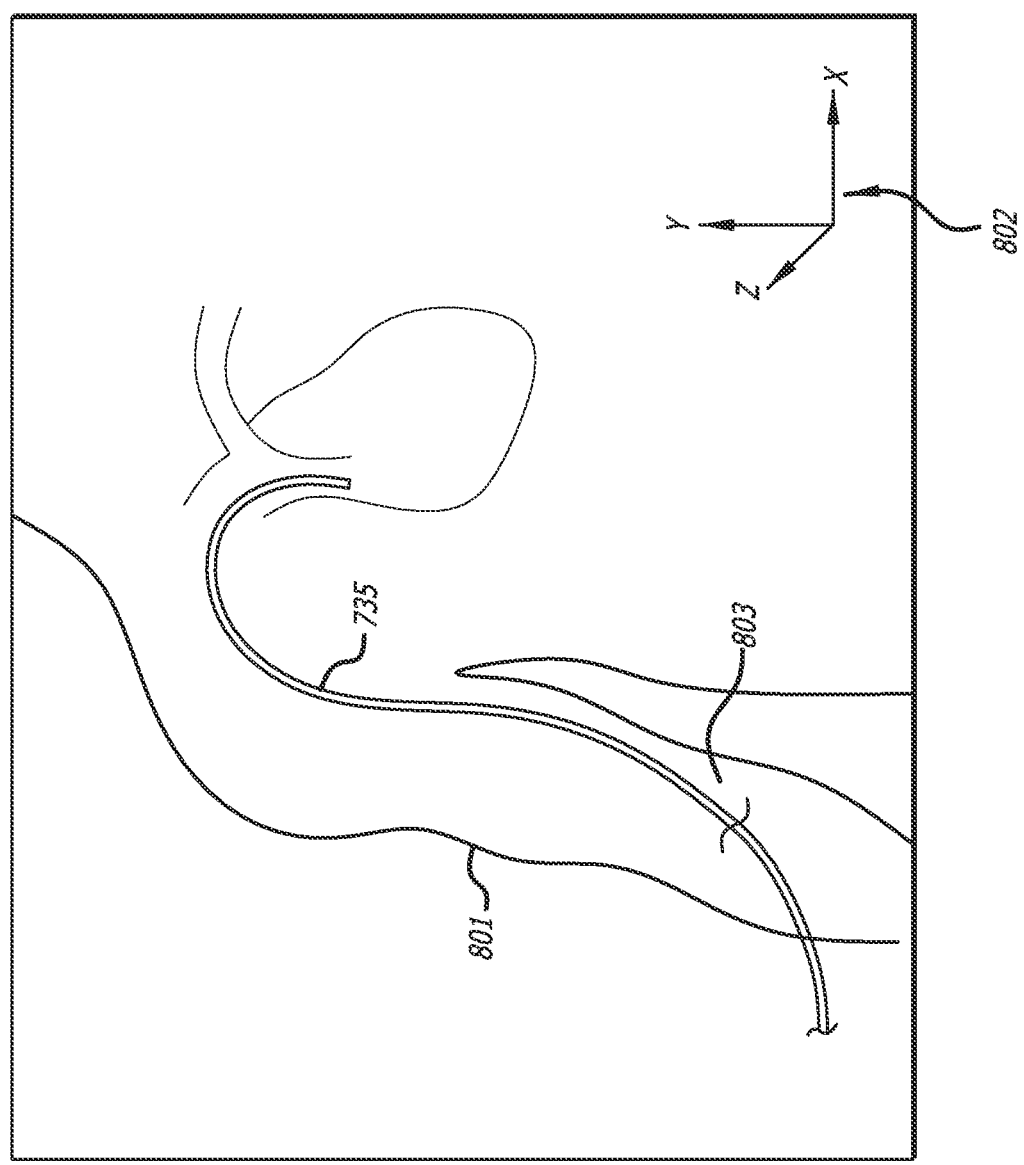

REFERENCE PLANE FOR MEDICAL DEVICE PLACEMENT

PRIORITY

This application claims the benefit of priority to U.S. Provisional Application No. 63/271,630, filed Oct. 25, 2021, which is incorporated by reference in its entirety into this application.

BACKGROUND

In the past, certain intravascular guidance of medical devices, such as guidewires and catheters for example, have used fluoroscopic methods for tracking tips of the medical devices and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

Disclosed herein is a fiber optic shape sensing system and methods performed thereby where the system is configured to display an image of three-dimensional shape of a medical device using optical fiber technology. Further, the system is configured to define a reference frame for the three-dimensional shape to enable to the clinician to view an image the three-dimensional shape according to defined orientations of the three-dimensional shape.

SUMMARY

Briefly summarized, disclosed herein is a medical device system generally including a medical device coupled with a console. The medical device includes an optical fiber having one or more of core fibers, each of the one or more core fibers including a plurality of sensors distributed along a longitudinal length of a corresponding core fiber, each sensor of the plurality of sensors configured to: (i) reflect a light signal of a different spectral width based on received incident light, and (ii) change a characteristic of the reflected light signal based on strain experienced by the optical fiber.

The console includes one or more processors and a non-transitory computer-readable medium having stored thereon logic, when executed by the one or more processors, causes performance of operations of the system. The operations include: (i) providing an incident light signal to the optical fiber, (ii) receiving reflected light signals of different spectral widths of the incident light by one or more of the plurality of sensors (iii) processing the reflected light signals associated with the one or more of core fibers to determine a three-dimensional (3D) shape of the optical fiber, (iv) detecting a predetermined subshape of the 3D shape, and (v) defining a reference plane in accordance with the predetermined subshape, where the reference plane defines a viewing perspective of the 3D shape. In further embodiments, the operations include rendering an image of the 3D shape on a display of the system in accordance with the reference plane.

In some embodiments, detecting the predetermined subshape includes comparing a subshape of the 3D shape with a stored predetermined subshape in memory and as a result of the comparison, identifying the subshape as the predetermined subshape of the 3D shape. A plurality of stored predetermined subshapes may be included in the memory, and the operations may further include selecting the stored predetermined subshape from the plurality of stored predetermined subshapes in memory.

The predetermined subshape may be defined by a predetermined pathway of the medical device. In some embodiments, the medical device is configured for insertion within a patient body, and the predetermined pathway includes a predetermined anatomical pathway of the medical device. The operations may include receiving input from a clinician defining the anatomical pathway for the medical device and selecting the stored predetermined subshape according to the input from the clinician. In some embodiments, the input from the clinician includes a location of an insertion site for the medical device. In some embodiments, the predetermined anatomical pathway may extend along one or more of a basilic vein, a subclavian vein, an innominate vein, or a superior vena cava of the patient.

In some embodiments, the predetermined subshape is defined by a predetermined pathway of the medical device external to the patient such as a predetermined pathway defined by a subshape guide of the medical device, where in use, the medical device is disposed within a pathway of the subshape guide. In some embodiments, the clinician may insert the medical device within the pathway of the subshape guide during use of the system.

The subshape guide may be included within a package of the medical device and in some embodiments, the subshape guide may be formed integral to the package. In use, the subshape guide may be attached to the patient to maintain an orientation of the predetermined subshape with respect to the patient.

In some embodiments, defining the reference plane includes identifying a pair of shape segments of the predetermined subshape and determining a plane in parallel with both shape segments.

In some embodiments, the system further includes a device guide including a lumen extending along a straight section of the device guide. In use, the medical device is inserted within the lumen, and the operations further include calibrating the optical fiber in accordance with the straight section.

In some embodiments, the medical device is one of an introducer wire, a guidewire, a stylet, a stylet within a needle, a needle with the optical fiber inlayed into a cannula of the needle or a catheter with the optical fiber inlayed into one or more walls of the catheter.

Also disclosed herein is a method for detecting placement of a medical device within a patient body. The method includes providing by a system an incident light signal to an optical fiber included within the medical device, wherein the optical fiber includes one or more of core fibers, each of the one or more of core fibers including a plurality of reflective gratings distributed along a longitudinal length of a corresponding core fiber and each of the plurality of reflective gratings being configured to (i) reflect a light signal of a different spectral width based on received incident light, and (ii) change a characteristic of the reflected light signal based on strain experienced by the optical fiber.

The method further includes: (i) receiving reflected light signals of different spectral widths of the incident light by one or more of the plurality of sensors, (ii) processing the reflected light signals associated with the one or more of core fibers to determine a three-dimensional (3D) shape of the optical fiber, (iii) detecting a predetermined subshape of the 3D shape, and (iv) defining a reference plane in accordance with the predetermined subshape, where the reference plane defines a viewing perspective of the 3D shape. In further embodiments, the method further includes rendering an image of the 3D shape on a display of the system in accordance with the reference plane.

In some embodiments, detecting the predetermined subshape includes comparing a subshape of the 3D shape with a stored predetermined subshape in memory of the system and as a result of the comparison, identifying the subshape as the predetermined subshape of the 3D shape. A plurality of stored predetermined subshapes may be included in memory of the system, and the method may further include selecting the stored predetermined subshape from the plurality of stored predetermined subshapes in memory.

In some embodiments of the method, the predetermined subshape is defined by a predetermined pathway of the medical device and the predetermined pathway may include a predetermined anatomical pathway of the medical device.

The method may further include receiving input from a clinician defining the anatomical pathway for the medical device and selecting the stored predetermined subshape according to the input from the clinician. The input from the clinician may include a location of an insertion site for the medical device. In some embodiments, the predetermined anatomical pathway extends along one or more of a basilic vein, a subclavian vein, an innominate vein, or a superior vena cava of the patient. In other embodiments of the method, the predetermined subshape is defined by a predetermined pathway of the medical device external to the patient.

The method may further include identifying a pair of shape segments of the predetermined subshape and determining a plane in parallel with both shape segments.

In some embodiments of the method, the medical device is inserted within a lumen of a medical device guide of the system, and the method further includes calibrating the optical fiber in accordance with a straight section of the medical device guide.

In some embodiments of the method, the medical device is one of an introducer wire, a guidewire, a stylet, a stylet within a needle, a needle with the optical fiber inlayed into a cannula of the needle or a catheter with the optical fiber inlayed into one or more walls of the catheter.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A is a first exemplary embodiment of the stylet of FIG. 1A supporting both an optical and electrical signaling in accordance with some embodiments;

FIG. 3B is a cross sectional view of the stylet of FIG. 3A in accordance with some embodiments;

FIG. 4A is a second exemplary embodiment of the stylet of FIG. 1B in accordance with some embodiments;

FIG. 4B is a cross sectional view of the stylet of FIG. 4A in accordance with some embodiments;

FIG. 7B illustrates the 3D shape of FIG. 7A according to a reference plane in accordance with some embodiments;

FIG. 8 is an exemplary screen shot of image of the 3D shape of FIGS. 7A-7B in accordance with some embodiments;

DETAILED DESCRIPTION

Figure 1A:
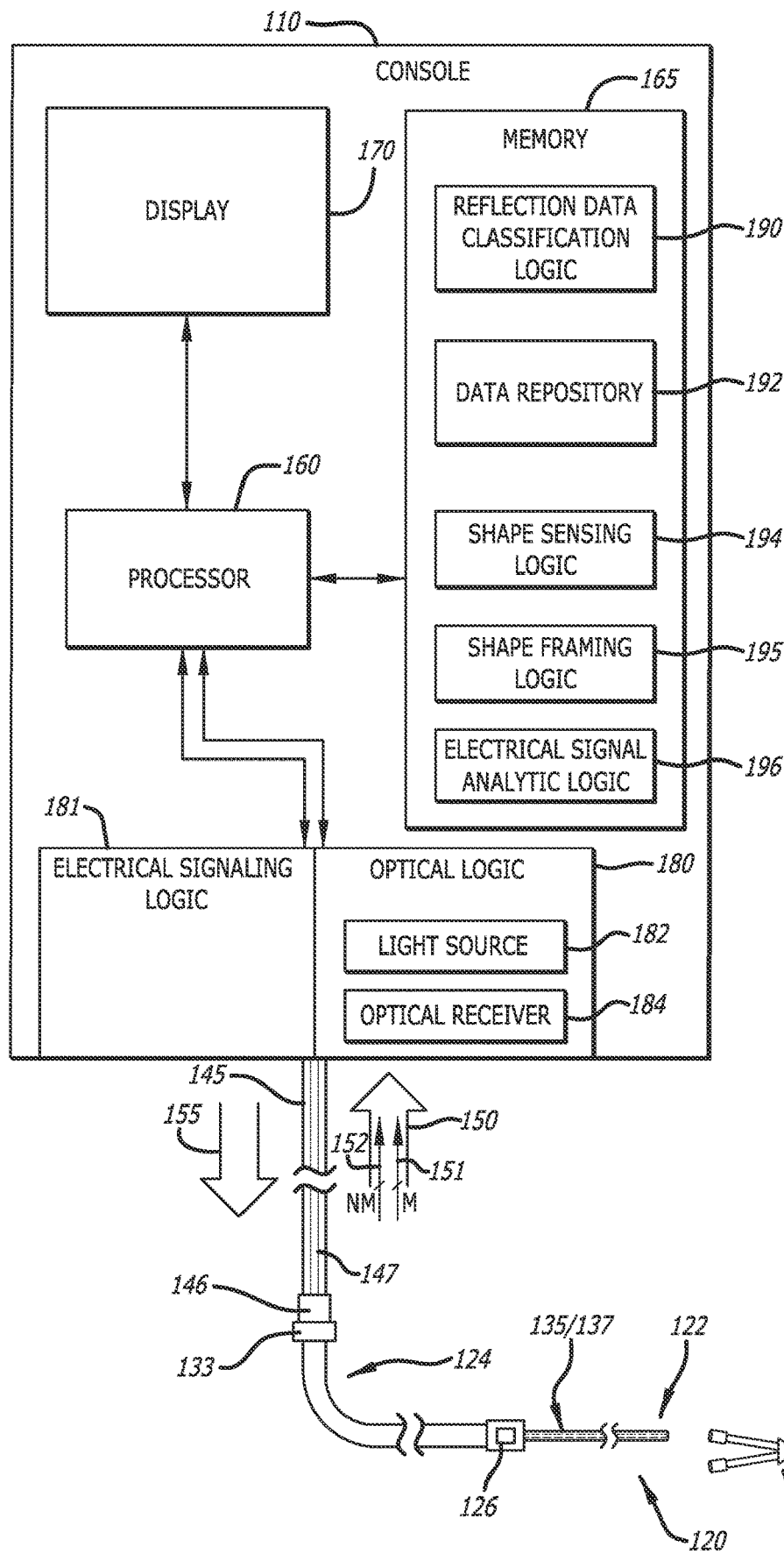
FIG. 1A is an illustrative embodiment of a medical instrument monitoring system including a medical instrument with optic shape sensing capabilities in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified.

Moreover, sub-routines or only a portion of a method described herein may be a separate method within the scope of this disclosure. Stated otherwise, some methods may include only a portion of the steps described in a more detailed method.

The phrases "connected to" and "coupled with" refer to any form of interaction between two or more entities, including mechanical, electrical, magnetic, electromagnetic, fluid, and optical interaction. Two components may be connected to or coupled with each other even though they are not in direct contact with each other. For example, two components may be coupled with each other through an intermediate component.

Referring to FIG. 1A, an illustrative embodiment of a medical instrument monitoring system including a medical instrument (sometimes referred to herein as a medical device) with optic shape sensing and fiber optic-based oximetry capabilities is shown in accordance with some embodiments. As shown, the system 100 generally includes a console 110 and a medical device in the form of a stylet assembly 119 communicatively coupled to the console 110. For this embodiment, the stylet assembly 119 includes an elongate probe (e.g., stylet) 120 on its distal end 122 and a console connector 133 on its proximal end 124. The console connector 133 enables the stylet assembly 119 to be operably connected to the console 110 via an interconnect 145 including one or more optical fibers 147 (hereinafter, "optical fiber(s)") and a conductive medium terminated by a single optical/electric connector 146 (or terminated by dual connectors. Herein, the connector 146 is configured to engage (mate) with the console connector 133 to allow for the propagation of light between the console 110 and the stylet assembly 119 as well as the propagation of electrical signals from the stylet 120 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Pat. No. 10,992,078, the entire contents of which are incorporated by reference herein. The processor 160, with access to the memory 165 (e.g., non-volatile memory or non-transitory, computer-readable medium), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. Although not shown, a user interface is configured to provide user control of the console 110.

In further embodiments, as an alternative to the display 170, the console 110 may be coupled with a virtual reality or augmented reality system (not shown). Such a system may provide an enhanced visualization of the 3D representations shown and described below.

For both of these embodiments, the content depicted by the display 170 may change according to which mode the stylet 120 is configured to operate: optical, TLS, ECG, or another modality. In TLS mode, the content rendered by the display 170 may constitute a two-dimensional (2D) or three-dimensional (3D) representation of the physical state (e.g., length, shape, form, and/or orientation) of the stylet 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below.

According to one embodiment of the disclosure, an activation control 126, included on the stylet assembly 119, may be used to set the stylet 120 into a desired operating mode and selectively alter operability of the display 170 by the clinician to assist in medical device placement. For example, based on the modality of the stylet 120, the display 170 of the console 110 can be employed for optical modality-based guidance during catheter advancement through the vasculature or TLS modality to determine the physical state (e.g., length, form, shape, orientation, etc.) of the stylet 120. In one embodiment, information from multiple modes, such as optical, TLS or ECG for example, may be displayed concurrently (e.g., at least partially overlapping in time).

Referring still to FIG. 1A, the optical logic 180 is configured to support operability of the stylet assembly 119 and enable the return of information to the console 110, which may be used to determine the physical state associated with the stylet 120 along with monitored electrical signals such as ECG signaling via an electrical signaling logic 181 that supports receipt and processing of the received electrical signals from the stylet 120 (e.g., ports, analog-to-digital conversion logic, etc.). The physical state of the stylet 120 may be based on changes in characteristics of the reflected light signals 150 received at the console 110 from the stylet 120. The characteristics may include shifts in wavelength caused by strain on certain regions of the core fibers integrated within an optical fiber core 135 positioned within or operating as the stylet 120, as shown below. As discussed herein, the optical fiber core 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the stylet 120, and also that of a catheter 121 configured to receive the stylet 120.

According to one embodiment of the disclosure, as shown in FIG. 1A, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the multi-core optical fiber core 135 within the stylet 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 120, and (ii) translate the reflected light signals 150 into reflection data (from repository 192), namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data (from repository 192) to the memory 165 for storage and processing by reflection data classification logic 190. The reflection data classification logic 190 may be configured to: (i) identify which core fibers pertain to which of the received reflection data (from repository 192) and (ii) segregate the reflection data stored with a repository 192 provided from reflected light signals 150 pertaining to similar regions of the stylet 120 or spectral widths into analysis groups. The reflection data for each analysis group is made available to shape sensing logic 194 for analytics.

According to one embodiment of the disclosure, the shape sensing logic 194 is configured to compare wavelength shifts measured by sensors deployed in each periphery core fiber at the same measurement region of the stylet 120 (or same spectral width) to the wavelength shift at a center core fiber of the multi-core optical fiber 135 positioned along central axis and operating as a neutral axis of bending. From these analytics, the shape sensing logic 194 may determine the shape the core fibers have taken in 3D space and may further determine the current physical state of the catheter 121 in 3D space for rendering on the display 170.

According to one embodiment of the disclosure, the shape sensing logic 194 may generate a rendering of the current physical state of the stylet 120 (and potentially the catheter 121), based on heuristics or run-time analytics. For example, the shape sensing logic 194 may be configured in accordance with machine-learning techniques to access a data store (library) with pre-stored data (e.g., images, etc.) pertaining to different regions of the stylet 120 (or catheter 121) in which reflected light from core fibers have previously experienced similar or identical wavelength shifts. From the pre-stored data, the current physical state of the stylet 120 (or catheter 121) may be rendered. Alternatively, as another example, the shape sensing logic 194 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 120 (and/or catheter 121), especially to enable guidance of the stylet 120, when positioned at a distal tip of the catheter 121, within the vasculature of the patient and at a desired destination within the body.

The console 110 may further include electrical signaling logic 181, which is positioned to receive one or more electrical signals from the stylet 120. The stylet 120 is configured to support both optical connectivity as well as electrical connectivity. The electrical signaling logic 181 receives the electrical signals (e.g., ECG signals) from the stylet 120 via the conductive medium. The electrical signals may be processed by electrical signal logic 196, executed by the processor 160, to determine ECG waveforms for display.

Figure 1B:
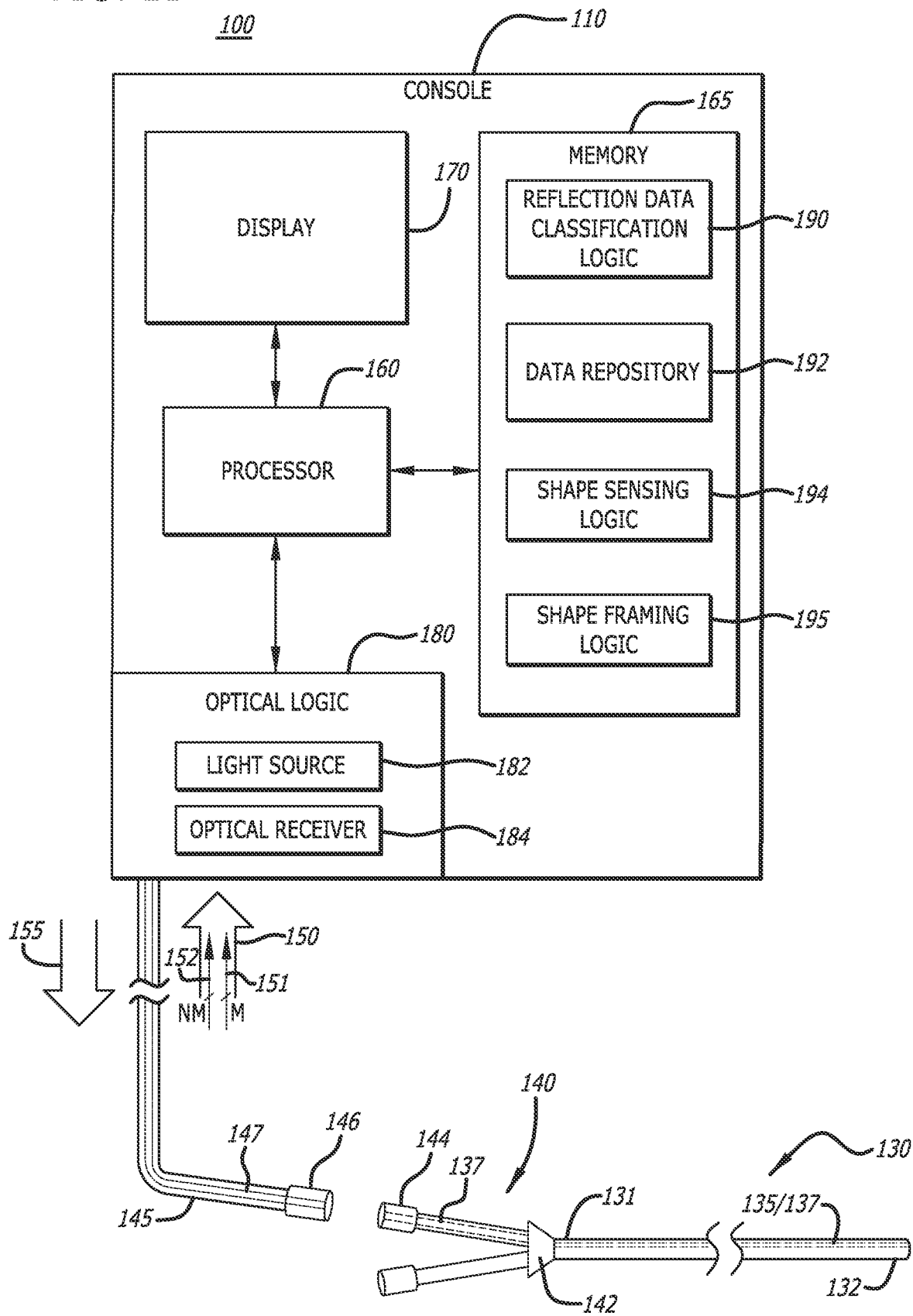
FIG. 1B is an alternative illustrative embodiment of the medical instrument monitoring system 100 in accordance with some embodiments.

Referring to FIG. 1B, an alternative exemplary embodiment of a medical instrument monitoring system 100 is shown. Herein, the medical instrument monitoring system 100 features a console 110 and a medical instrument 130 communicatively coupled to the console 110. For this embodiment, the medical instrument 130 corresponds to a catheter, which features an integrated tubing with two or more lumen extending between a proximal end 131 and a distal end 132 of the integrated tubing. The integrated tubing (sometimes referred to as "catheter tubing") is in communication with one or more extension legs 140 via a bifurcation hub 142. An optical-based catheter connector 144 may be included on a proximal end of at least one of the extension legs 140 to enable the catheter 130 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 130 and integrated into the tubing. Alternatively, a different combination of connectors, including one or more adapters, may be used to optically connect the optical fiber(s) 147 to the core fibers 137 within the catheter 130. The core fibers 137 deployed within the catheter 130 as illustrated in FIG. 1B include the same characteristics and perform the same functionalities as the core fibers 137 deployed within the stylet 120 of FIG. 1A.

The optical logic 180 is configured to support graphical rendering of the catheter 130, most notably the integrated tubing of the catheter 130, based on characteristics of the reflected light signals 150 received from the catheter 130. The characteristics may include shifts in wavelength caused by strain on certain regions of the core fibers 137 integrated within (or along) a wall of the integrated tubing, which may be used to determine (through computation or extrapolation of the wavelength shifts) the physical state of the catheter 130, notably its integrated tubing or a portion of the integrated tubing such as a tip or distal end.

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing. Herein, the optical receiver 184 is configured to: (i) receive returned optical signals, namely reflected light signals 150 received from optical fiber-based reflective gratings (sensors) fabricated within each of the core fibers 137 deployed within the catheter 130, and (ii) translate the reflected light signals 150 into reflection data (from repository 192), namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 130 and reflected light signals 152 provided from sensors positioned in the outer core fibers of the catheter 130, as described below.

As noted above, the shape sensing logic 194 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 194 may determine the shape the core fibers have taken in 3D space and may further determine the current physical state of the catheter 130 in 3D space for rendering on the display 170.

According to one embodiment of the disclosure, the shape sensing logic 194 may generate a rendering of the current physical state of the catheter 130, especially the integrated tubing, based on heuristics or run-time analytics. For example, the shape sensing logic 194 may be configured in accordance with machine-learning techniques to access a data store (library) with pre-stored data (e.g., images, etc.) pertaining to different regions of the catheter 130 in which the core fibers 137 experienced similar or identical wavelength shifts. From the pre-stored data, the current physical state of the catheter 130 may be rendered. Alternatively, as another example, the shape sensing logic 194 may be configured to determine, during run-time, changes in the physical state of each region of the catheter 130, notably the tubing, based on at least (i) resultant wavelength shifts experienced by the core fibers 137 and (ii) the relationship of these wavelength shifts generated by sensors positioned along different outer core fibers at the same cross-sectional region of the catheter 130 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 130.

Figure 2:
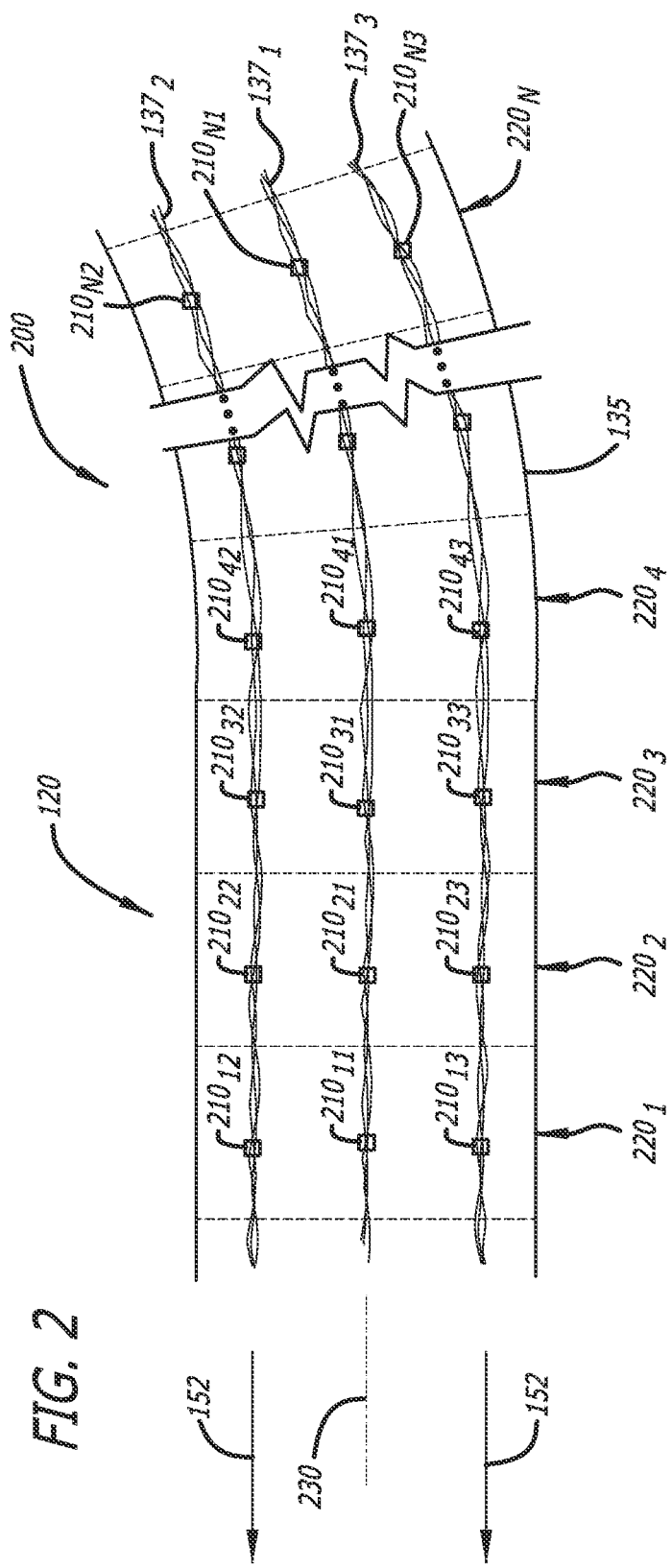
FIG. 2 is an exemplary embodiment of a structure of a section of the multi-core optical fiber included within the stylet 120 of FIG. 1A in accordance with some embodiments.

Referring to FIG. 2, an exemplary embodiment of a structure of a section of the multi-core optical fiber included within the stylet 120 of FIG. 1A is shown in accordance with some embodiments. The multi-core optical fiber section 200 of the multi-core optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ . . . $210_{N1}$-$210_{N4}$. Some or all of the cross-sectional regions $220_1$ . . . $220_N$ may be static (e.g., prescribed length) or may be dynamic (e.g., vary in size among the regions $220_1$ . . . $220_N$). A first core fiber $137_1$ is positioned substantially along a center (neutral) axis 230 while core fiber $137_2$ may be oriented within the cladding of the multi-core optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the stylet 120 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1 \ldots f_N$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the multi-core optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the stylet 120) based on wavelength shifts measured from the returned, reflected light. In particular, strain (e.g., compression or tension) applied to the multi-core optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the stylet 120 advances in the patient.

For example, with respect to the multi-core optical fiber section 200 of FIG. 2, in response to angular (e.g., radial) movement of the stylet 120 is in the left-veering direction, the fourth core fiber $137_4$ (see FIG. 3A) of the multi-core optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the stylet 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 135. These degrees of wavelength change may be used to extrapolate the physical state of the stylet 120. The reflected light signals 150 are reflected back to the console 110 via individual paths over a particular core fiber $137_1$-$137_M$.

Referring to FIG. 3A, a first exemplary embodiment of the stylet of FIG. 1A supporting both an optical and electrical signaling is shown in accordance with some embodiments. Herein, the stylet 120 features a centrally located multi-core optical fiber 135, which includes a cladding 300 and a plurality of core fibers $137_1$-$137_M$ (M≥2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M>4) may be deployed to provide a more detailed 3D sensing of the physical state (e.g., shape, etc.) of the multi-core optical fiber 135 and the stylet 120 deploying the optical fiber 135.

For this embodiment of the disclosure, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the stylet 120, as a greater spacing may provide a lesser rigidity, and thereby, a more pliable stylet 120.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable 3D sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the stylet 120, the braided tubing 310 provides mechanical integrity to the multi-core optical fiber 135 and operates as a conductive pathway for electrical signals. For example, the braided tubing 310 may be exposed to a distal tip of the stylet 120. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Referring to FIG. 4A, a second exemplary embodiment of the stylet of FIG. 1B is shown in accordance with some embodiments. Referring now to FIG. 4A, a second exemplary embodiment of the stylet 120 of FIG. 1B supporting both an optical and electrical signaling is shown. Herein, the stylet 120 features the multi-core optical fiber 135 described above and shown in FIG. 3A, which includes the cladding 300 and the first plurality of core fibers $137_1$-$137_M$ (M≥3; M=4 for embodiment) residing within the corresponding plurality of lumens $320_1$-$320_M$. For this embodiment of the disclosure, the multi-core optical fiber 135 includes the central core fiber $137_1$ residing within the first lumen $320_1$ formed along the first neutral axis 230 and the second plurality of core fibers $137_2$-$137_4$ residing within corresponding lumens $320_2$-$320_4$ positioned in different segments within the cross-sectional area 305 of the cladding 300. Herein, the multi-core optical fiber 135 is encapsulated within a conductive tubing 400. The conductive tubing 400 may feature a "hollow" conductive cylindrical member concentrically encapsulating the multi-core optical fiber 135.

Referring to FIGS. 4A-4B, operating as a conductive medium for the stylet 120 in the transfer of electrical signals (e.g., ECG signals) to the console, the conductive tubing 400 may be exposed up to a tip 410 of the stylet 120. For this embodiment of the disclosure, a conductive epoxy 420 (e.g., metal-based epoxy such as a silver epoxy) may be affixed to the tip 410 and similarly joined with a termination/connection point created at a proximal end 430 of the stylet 120. The cladding 300 and the conductive tubing 400, which is positioned concentrically surrounding a circumference of the cladding 300, are contained within the same insulating layer 440. The insulating layer 440 may be a protective conduit encapsulating both for the cladding 300 and the conductive tubing 400, as shown.

Figure 5A:
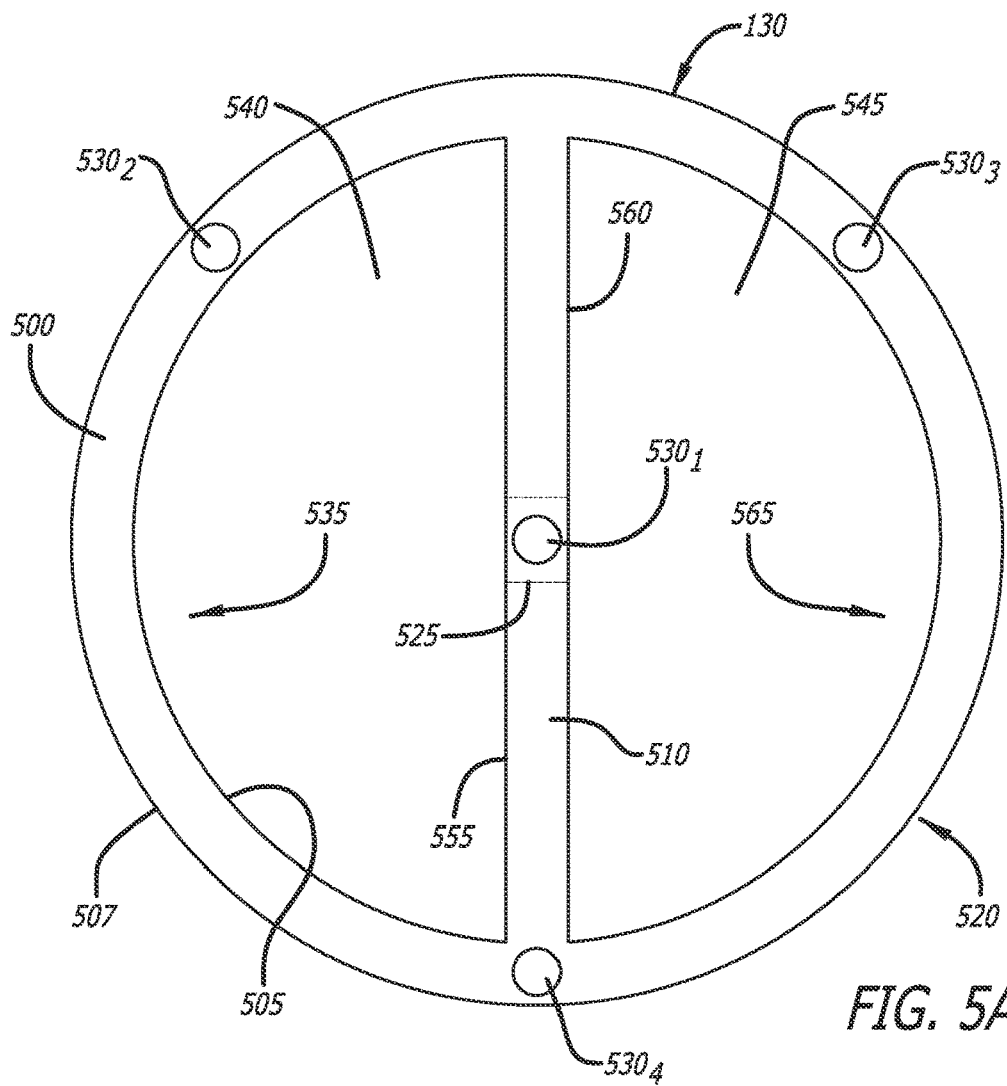
FIG. 5A is an elevation view of a first illustrative embodiment of a catheter including integrated tubing, a diametrically disposed septum, and micro-lumens formed within the tubing and septum in accordance with some embodiments.

Referring to FIG. 5A, an elevation view of a first illustrative embodiment of a catheter including integrated tubing, a diametrically disposed septum, and micro-lumens formed within the tubing and septum is shown in accordance with some embodiments. Herein, the catheter 130 includes integrated tubing, the diametrically disposed septum 510, and the plurality of micro-lumens $530_1$-$530_4$ which, for this embodiment, are fabricated to reside within the wall 500 of the integrated tubing of the catheter 130 and within the septum 510. In particular, the septum 510 separates a single lumen, formed by the inner surface 505 of the wall 500 of the catheter 130, into multiple lumen, namely two lumens 540 and 545 as shown. Herein, the first lumen 540 is formed between a first arc-shaped portion 535 of the inner surface 505 of the wall 500 forming the catheter 130 and a first outer surface 555 of the septum 510 extending longitudinally within the catheter 130. The second lumen 545 is formed between a second arc-shaped portion 565 of the inner surface 505 of the wall 500 forming the catheter 130 and a second outer surfaces 560 of the septum 510.

According to one embodiment of the disclosure, the two lumens 540 and 545 have approximately the same volume. However, the septum 510 need not separate the tubing into two equal lumens. For example, instead of the septum 510 extending vertically (12 o'clock to 6 o'clock) from a front-facing, cross-sectional perspective of the tubing, the septum 510 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 540 and 545 of the catheter 130 would have a different volume.

With respect to the plurality of micro-lumens $530_1$-$530_4$, the first micro-lumen $530_1$ is fabricated within the septum 510 at or near the cross-sectional center 525 of the integrated tubing. For this embodiment, three micro-lumens $530_2$-$530_4$ are fabricated to reside within the wall 500 of the catheter 130. In particular, a second micro-lumen $530_2$ is fabricated within the wall 500 of the catheter 130, namely between the inner surface 505 and outer surface 507 of the first arc-shaped portion 535 of the wall 500. Similarly, the third micro-lumen $530_3$ is also fabricated within the wall 500 of the catheter 130, namely between the inner and outer surfaces 505/507 of the second arc-shaped portion 555 of the wall 500. The fourth micro-lumen $530_4$ is also fabricated within the inner and outer surfaces 505/507 of the wall 500 that are aligned with the septum 510.

According to one embodiment of the disclosure, as shown in FIG. 5A, the micro-lumens $530_2$-$530_4$ are positioned in accordance with a "top-left" (10 o'clock), "top-right" (2 o'clock) and "bottom" (6 o'clock) layout from a front-facing, cross-sectional perspective. Of course, the micro-lumens $530_2$-$530_4$ may be positioned differently, provided that the micro-lumens $530_2$-$530_4$ are spatially separated along the circumference 520 of the catheter 130 to ensure a more robust collection of reflected light signals from the outer core fibers $570_2$-$570_4$ when installed. For example, two or more of micro-lumens (e.g., micro-lumens $530_2$ and $530_4$) may be positioned at different quadrants along the circumference 520 of the catheter wall 500.

Figure 5B:
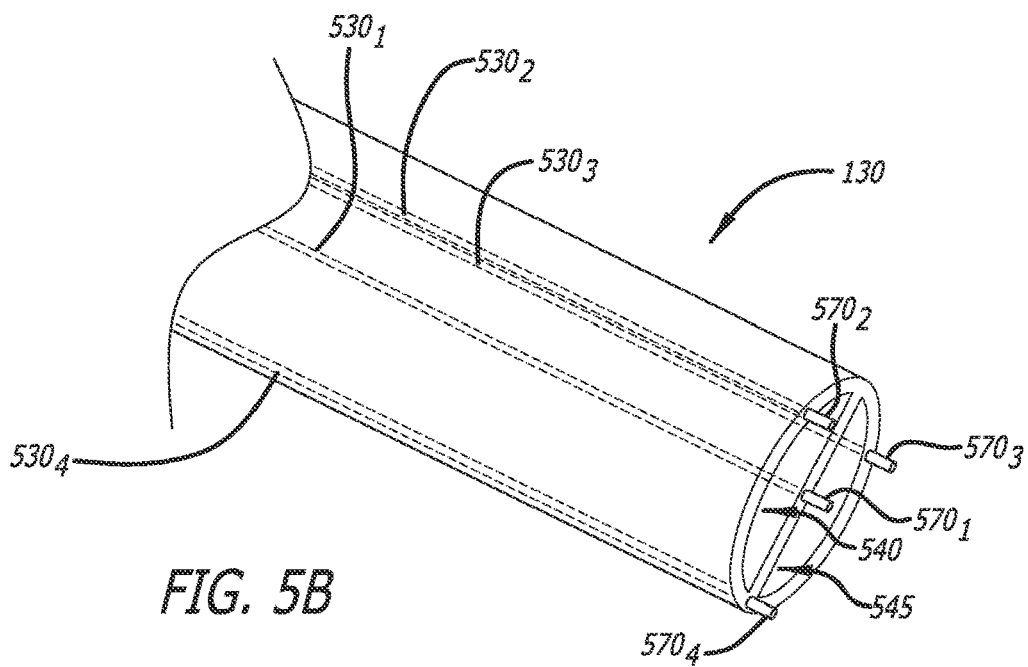
FIG. 5B is a perspective view of the first illustrative embodiment of the catheter of FIG. 5A including core fibers installed within the micro-lumens in accordance with some embodiments.

Referring to FIG. 5B, a perspective view of the first illustrative embodiment of the catheter of FIG. 5A including core fibers installed within the micro-lumens is shown in accordance with some embodiments. According to one embodiment of the disclosure, the second plurality of micro-lumens $530_2$-$530_4$ are sized to retain corresponding outer core fibers $570_2$-$570_4$, where the diameter of each of the second plurality of micro-lumens $530_2$-$530_4$ may be sized just larger than the diameters of the outer core fibers $570_2$-$570_4$. The size differences between a diameter of a single core fiber and a diameter of any of the micro-lumen $530_1$-$530_4$ may range between 0.001 micrometers (μm) and 1000 μm, for example. As a result, the cross-sectional areas of the outer core fibers $570_2$-$570_4$ would be less than the cross-sectional areas of the corresponding micro-lumens $530_2$-$530_4$. A "larger" micro-lumen (e.g., micro-lumen $530_2$) may better isolate external strain being applied to the outer core fiber $570_2$ from strain directly applied to the catheter 130 itself. Similarly, the first micro-lumen $530_1$ may be sized to retain the center core fiber $570_1$, where the diameter of the first micro-lumen $530_1$ may be sized just larger than the diameter of the center core fiber $570_1$.

As an alternative embodiment of the disclosure, one or more of the micro-lumens $530_1$-$530_4$ may be sized with a diameter that exceeds the diameter of the corresponding one or more core fibers $570_1$-$570_4$. However, at least one of the micro-lumens $530_1$-$530_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $530_1$-$530_4$ are sized with a diameter to fixedly retain the core fibers $570_1$-$570_4$.

Figure 6A:
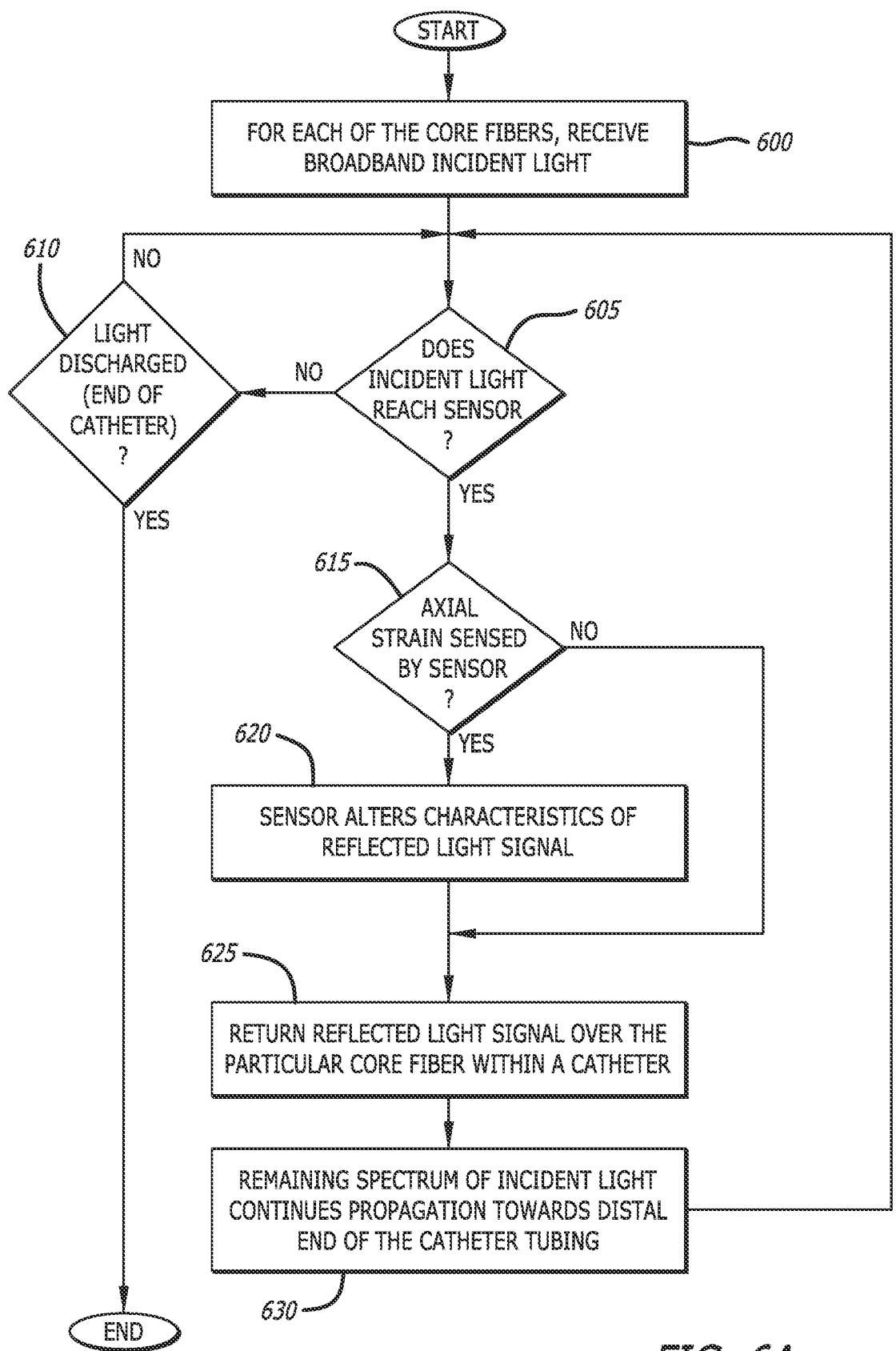
FIGS. 6A-6B are flowcharts of the methods of operations conducted by the medical instrument monitoring system of FIGS. 1A-1B to achieve optic 3D shape sensing, in accordance with some embodiments.
Figure 6B:
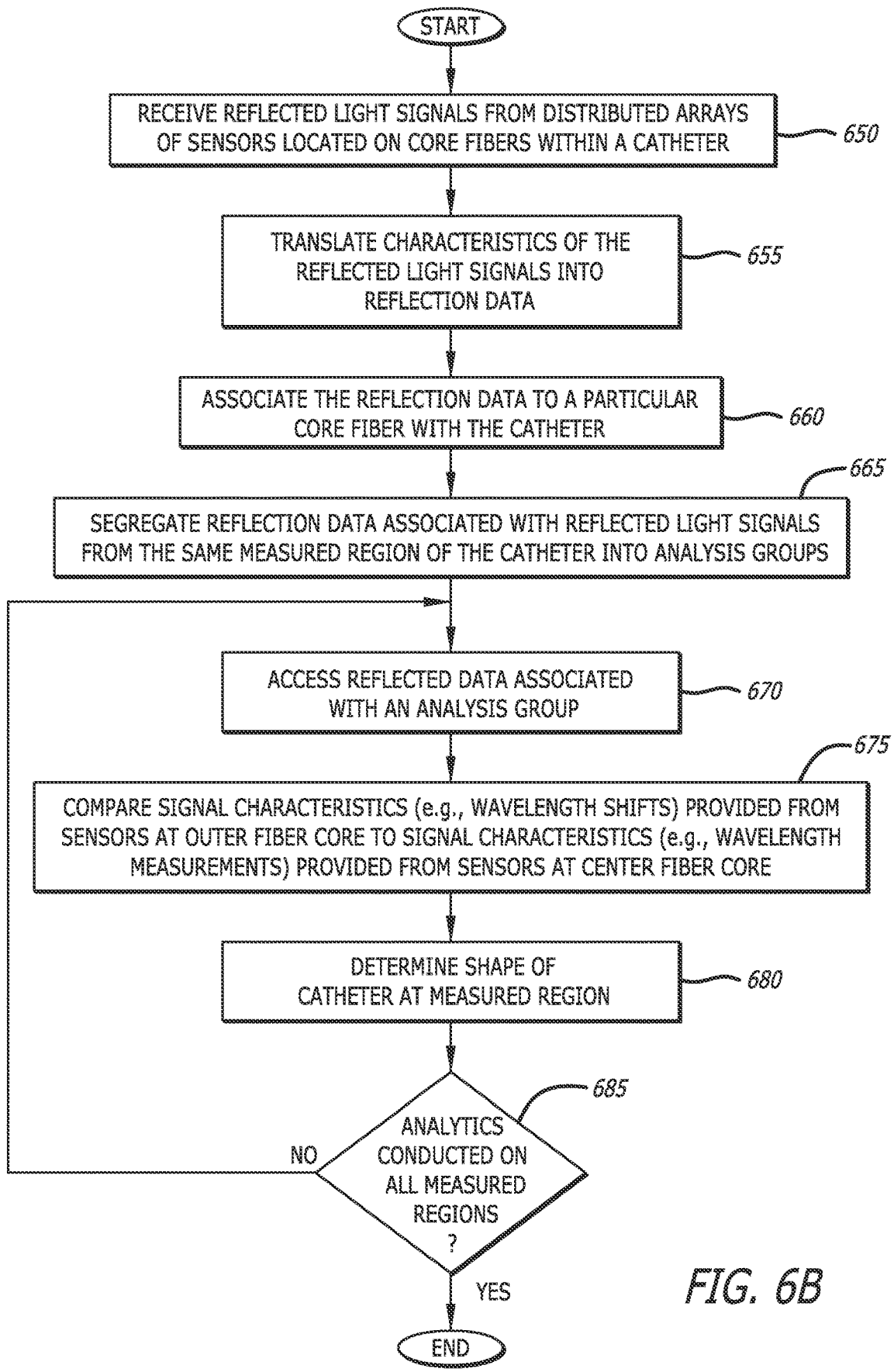

Referring to FIGS. 6A-6B, flowcharts of methods of operations conducted by the medical instrument monitoring system of FIGS. 1A-1B to achieve optic 3D shape sensing are shown in accordance with some embodiments. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors is distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounter other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within a catheter, such as the catheter of FIG. 1B. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From this analytics, on all analytic groups (e.g., reflected light signals from sensors in all or most of the core fibers), the shape sensing logic may determine the shape the core fibers have taken in 3D space, from which the shape sensing logic can determine the current physical state of the catheter in three-dimension space (blocks 680-685).

Figure 7A:
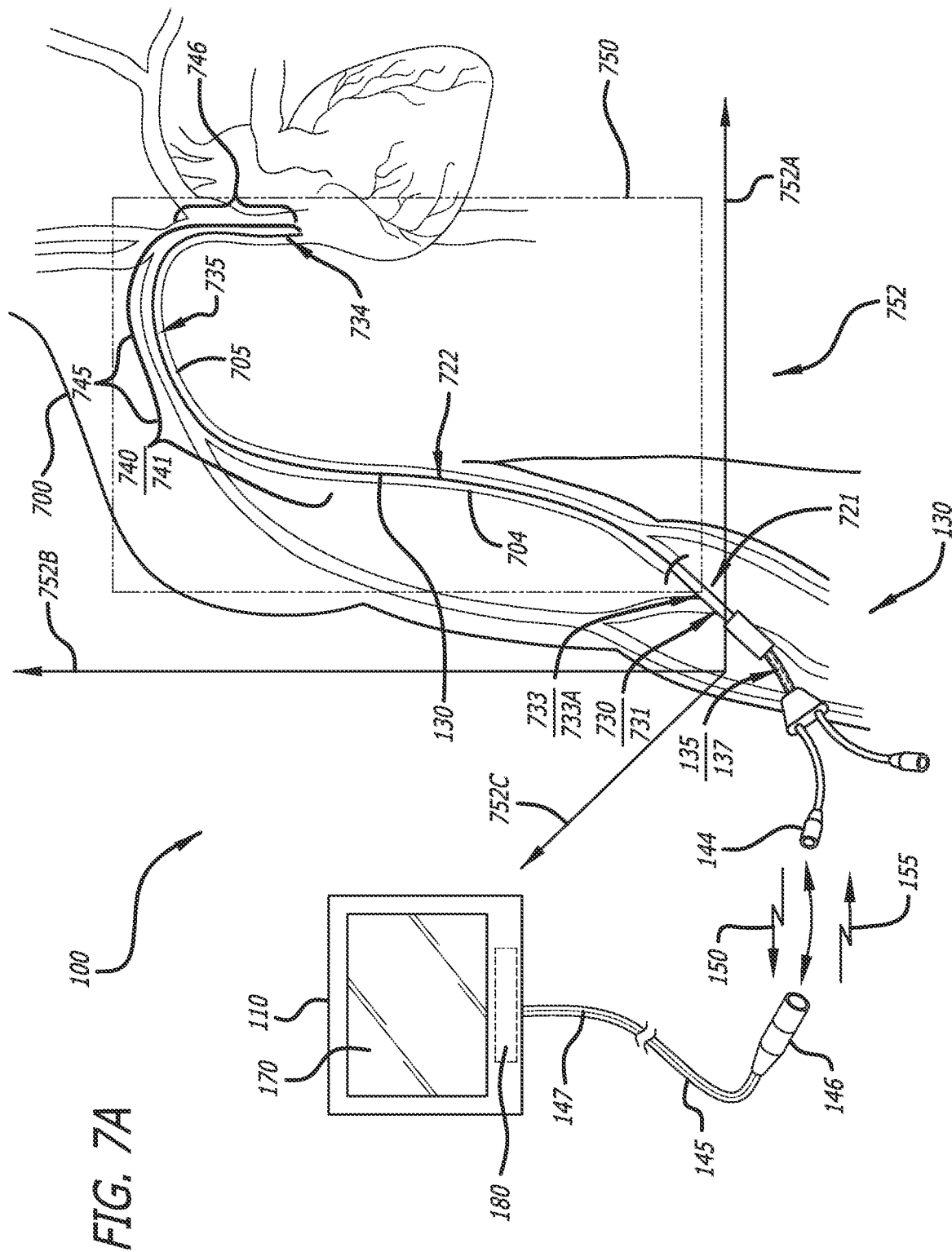
FIG. 7A is an exemplary embodiment of the medical instrument monitoring system of FIGS. 1A-1B during operation and insertion of the catheter into a patient in accordance with some embodiments.

Referring to FIG. 7A, an exemplary embodiment of the medical instrument monitoring system of FIG. 1B during operation and insertion of the catheter into a patient is shown in accordance with some embodiments. For illustrative purposes, FIG. 7A includes the 3D coordinate axis system 752 having a horizontal x-axis 752A pointing to the right, a vertical y-axis 752B pointing up, and a z-axis 752C pointing into the page to illustrate the 3D space surrounding the patient 700. Herein, the catheter 130 generally includes the integrated tubing of the catheter 130. A proximal portion 721 generally remains exterior to the patient 700 and a distal portion 722 generally resides within the patient 700 after placement is complete. The (integrated) catheter tubing of the catheter 130 may be advanced to a desired position within a patient vasculature 704 such that a distal end (or tip) 734 of the catheter tubing of the catheter 130 is proximate the patient's heart, such as in the lower one-third (⅓) portion of the Superior Vena Cava ("SVC"), for example. In some embodiments, various instruments may be disposed at the distal end 734 of the catheter 130 to measure pressure of blood in a certain heart chamber and in the blood vessels, view an interior of blood vessels, or the like. In alternative embodiments, such as those that utilize the stylet assembly of FIG. 1A and the catheter 121, such instruments may be disposed at a distal end of the stylet 120.

During advancement through the patient vasculature 704, the catheter tubing of the catheter 130 receives broadband incident light 155 from the console 110 via optical fiber(s) 147 within the interconnect 145, where the incident light 155 propagates along the core fibers 137 of the multi-core optical fiber 135 within the catheter tubing of the catheter 130. According to one embodiment of the disclosure, the connector 146 of the interconnect 145 terminating the optical fiber(s) 147 may be coupled to the optical-based catheter connector 144, which may be configured to terminate the core fibers 137 deployed within the catheter 130. Such coupling optically connects the core fibers 137 of the catheter 130 with the optical fiber(s) 147 within the interconnect 145. The optical connectivity is needed to propagate the incident light 155 to the core fibers 137 and return the reflected light signals 150 to the optical logic 180 within the console 110 over the interconnect 145. As described below in detail, the physical state of the catheter 130 may be ascertained based on analytics of the wavelength shifts of the reflected light signals 150 where the physical state includes a 3D shape 735 of the optical fiber 135. The 3D shape 735 generally comprises a curved line in 3D space consistent with the 3D shape of the catheter 130.

In some embodiments, the system 100 may include a guide 730 having a straight section 731. The guide 730 may be formed of an introducer having a lumen through which the catheter 130 is inserted. In use a distal portion of the guide 730 may be disposed inside the patient 700 while a proximal portion remains outside the patient 700. In some implementations, the guide 730, or more specifically the straight section 731, may facilitate a calibration of the optical fiber 135. For example, while a section 733 of the optical fiber 135 is disposed within the straight section 731, the shape framing logic 195 may interpret shape data pertaining to the shape 733A of the section 733 as defining a straight line.

The shape framing logic 195 may define a reference plane 750 in accordance with a subshape 740 where the subshape 740 is a portion of the 3D shape 735. The shape framing logic 195 may orient the reference plane 750 in the 3D space as represented by the coordinate axis system 752, and shape framing logic 195 may utilize the reference plane 750 for rendering an image of the 3D shape 735 on the display 170.

The shape framing logic 195 analyzes the subshape 740 to determine whether the subshape 740 is consistent in shape with a predetermined subshape that may be stored in the data repository 192. As used herein, the term "consistent in shape" may be that a first subshape and a second subshape match at least within a tolerance for a substantial percentage of the two subshapes. Detecting a predetermined shape, may include comparing the subshape 740 with a selected one of a plurality of stored predetermined subshapes in the memory (e.g., the data repository 192) to determine if the subshape 740 is effectively consistent with the selected one of the stored predetermined subshapes. With the subshape 740 determined to be consistent with a predetermined subshape in memory, the subshape 740 may then be defined as the predetermined subshape 741 of the 3D shape 735.

The plurality of stored predetermined subshapes may include a subset of stored predetermined subshapes pertaining to anatomical pathways through the body of the patient 700. For example, a stored predetermined subshape may pertain to an anatomical pathway of the patient vasculature 704 including one or more of a basilic vein, a subclavian vein, an innominate vein, or a superior vena cava.

Selecting a stored predetermined subshape from the plurality of predetermined subshapes stored in memory may include receiving input from a clinician where the input defines the anatomical pathway. For example, the input may include an insertion site for the medical instrument.

According to one embodiment of the disclosure, the shape framing logic 195 may generate a rendering of the current position and orientation of the catheter 130 based on heuristics or run-time analytics. For example, the shape framing logic 195 may be configured in accordance with machine-learning (ML) techniques to access the stored predetermined shapes in the data repository 192 pertaining to different anatomical pathways of the catheter 130. For example, a machine-learning model may be trained, using the stored predetermined shapes as training data, to generate scores of predetermined subshapes of the catheter 130 disposed along various anatomical pathways (e.g., anatomical pathways of patients of different sizes), where the score represents a probability that a particular predetermined subshape of the 3D shape corresponds to a stored predetermined subshape in the data repository 192. The ML model may be configured to receive predetermined subshape data and provide a score for the predetermined subshape.

In some embodiments, the shape framing logic 195 may define the reference plane 750 in accordance with two or more points or segments of the predetermined subshape 741. According to one embodiment, the shape framing logic 195 may identify the two segments 745, 746 of the predetermined subshape 741 for defining the reference plane 750. The segments 745, 746 may each effectively define a line segment where the segments 745, 746 are not collinear. In some embodiments, the shape framing logic 195 may utilize a cross-product geometric technique to define a normal line that is perpendicular to both segments 745, 746 and then define the reference plane 750 as perpendicular to the normal line. In other embodiments, the shape framing logic 195 may define the reference plane 750 according to a geometric technique utilizing a line defined by one of the two segments 745, 746 and a point disposed along the other segment. In still other embodiments, the shape framing logic 195 may define the reference plane 750 according to a geometric technique utilizing a line defined by one of the two segments 745, 746 and a direction defined by the other segment. As may be appreciated by one of ordinary skill, other geometric techniques may be utilized to define the plane 750 in accordance with the 3D shape 735.

With further reference to FIG. 7A, the catheter 130 is illustrated in accordance with a front view of the patient 700 where the front side of the patient 700 may be parallel with the x-y plane of the coordinate axis system 752. As such, the 3D shape 735 is similarly illustrated in accordance with a front view of the patient 700. In some instances, the reference plane 750 may be substantially parallel with the front side of the patient 700. Therefore, a front view image of the 3D shape 735 may be substantially consistent with viewing the 3D shape 735 at angle perpendicular to the reference plane 750.

FIG. 7B illustrates the 3D shape 735 in 3D space where the 3D space is again illustrated as the 3D coordinate axis system 752. The shape framing logic 195 may define the reference plane 750 to establish a viewing reference of an image of the 3D shape 735 on the display 170. For illustrative purposes, the reference plane 750 is shown in accordance with the 3D coordinate axis system 752 having a horizontal x-axis 752A pointing to the right, a vertical y-axis 752B pointing up, and a z-axis 752C pointing into the page. In the illustrated embodiment, the reference plane 750 is oriented so that the reference plane 750 is in parallel with the x-y plane. As such, a front view of the 3D shape 735 is defined by a viewing reference along the z-axis 752C.

In some embodiments, the shape framing logic 195 may lock the orientation of the reference plane 750 to the 3D space, i.e., to the illustrated 3D coordinate axis system 752. In other words, once the reference plane 750 is defined, movement/reorientation of the 3D shape 735 in 3D space, as may be caused by movement of the patient 700, may cause a corresponding movement/reorientation of the 3D shape 735 with respect to the reference plane 750.

In further embodiments, the shape framing logic 195 may lock the reference plane 750 to the predetermined subshape 741. As such, the shape framing logic 195 may be configured to render an image of the 3D shape 735 from any viewing reference. In other words, in response to input from the clinician, the shape framing logic 195 may reorient the reference plane 750, to render an image of the 3D shape 735 from a different viewing reference, such as from the top, right side, etc., for example. Viewing the 3D shape 735 from any angle with respect to the reference frame 750 as may be defined by the operator via the input device. In still further embodiments, the shape framing logic 195 may selectively lock the reference plane 750 to the 3D space or the predetermined subshape 741 in accordance with input from the clinician. In still other embodiments, the shape framing logic 195 may continuously define reference plane 750 according to the predetermined subshape 741 during use of the system 100.

FIG. 8 illustrates an exemplary screen shot 800 showing an image of the 3D shape 735 of FIGS. 7A, 7B rendered according to the reference plane 750. In some embodiments, the screen shot 800 may include a representation 801 of a patient body including the catheter insertion site 803. For example, in the illustrated embodiment, the representation 801 includes an outline of a typical patient body as may be viewed from the front to indicate the orientation of the 3D shape 735. In some embodiments, the representation 801 may include representations of other body parts, such as the heart as illustrated. In still other embodiments, the screen shot 800 may include indicia 801 to indicate the orientation of the 3D shape 735 as defined by the reference frame 751, such as a coordinate axis system, for example. In the screen shot 800, the image of the 3D shape 735 is consistent with the reference plane 750 in parallel with the screen of the display 170 defining a front view of the 3D shape 735. However, images of the 3D shape 735 are not limited to the front view. Although not shown, the shape framing logic 195 may facilitate rendering of images of the 3D shape 735 at any orientation (from any viewing reference) via input from the clinician as discussed above. As such, the shape framing logic 195 may shift the orientation of the representation 801 and/or the indica 802 to provide indication to the clinician as to the rendered orientation of the 3D shape 735.

In some embodiments, the system 100 may be communicatively coupled with an imaging system (e.g., ultrasound, MRI, X-ray, etc., not shown), and the shape framing logic 195 may facilitate rendering the image of the 3D shape 735 along with an image of patient 700. In some instances, the clinician may orient and/or position the image of the 3D shape 735 to position a portion of the 3D shape 735, such as a catheter tip 735, for example, at a specific location relative to an image of the patient 700. As the imaging system may include an image of the medical device directly, such an image may facilitate visual comparison between the 3D shape 735 and the image of the medical device. In some embodiments, the shape framing logic 195 may align a portion the 3D shape 735 with a corresponding portion of the medical device within the image of the patient 700.

In further embodiments, other device location or tracking modalities may be coupled with the system 100 and employed to indicate a position of the catheter 130. Such modalities may include ECG signal monitoring as described above and magnetic field sensing such as described in U.S. Pat. No. 5,099,845 entitled "Medical Instrument Location Means," which is incorporated herein by reference in its entirety. As such, the system 100 may render images or information on the display 170 pertaining to device location or tracking data in combination with the image of the 3D shape 735.

Figure 9A:
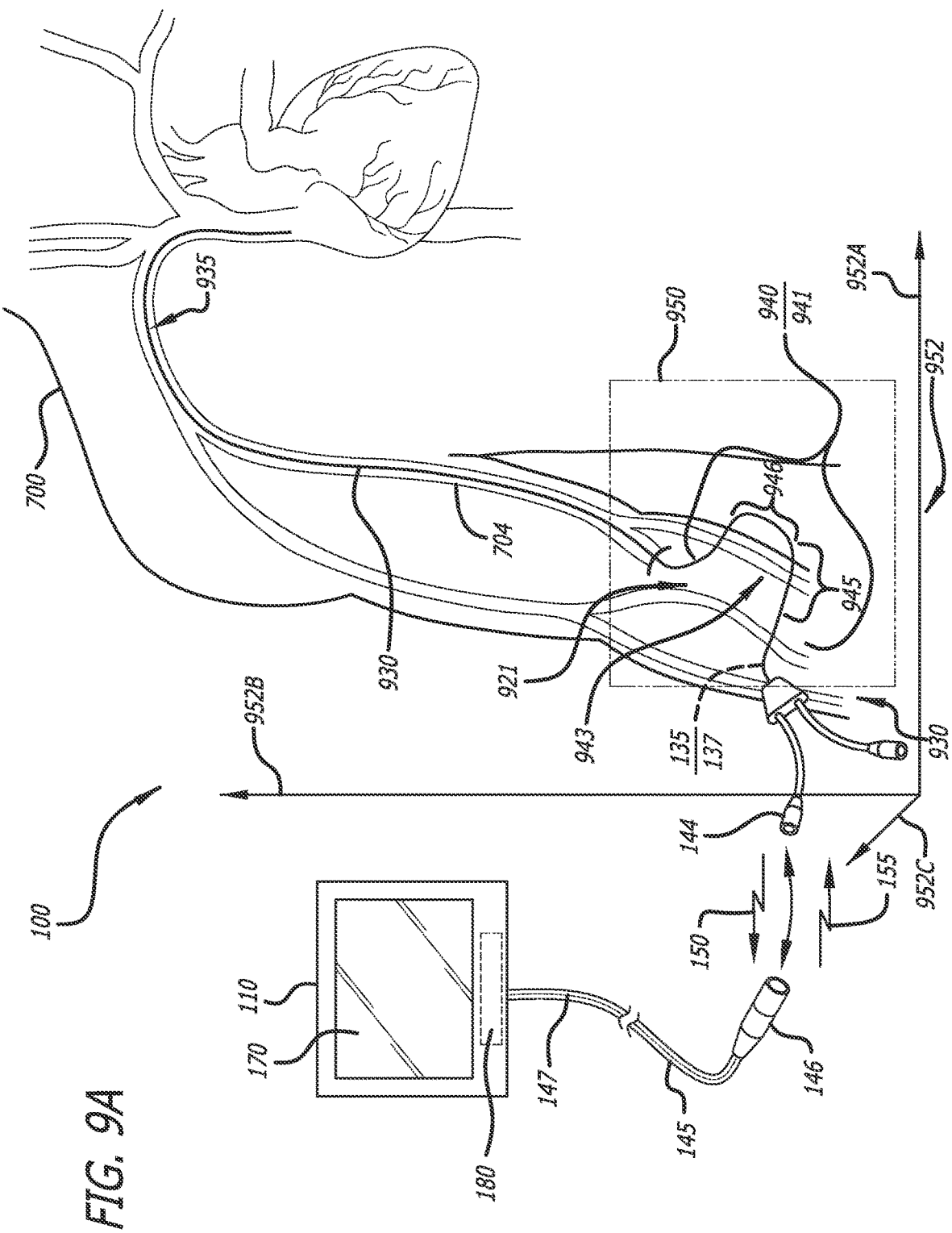
FIG. 9A is an illustration of a second exemplary implementation of the system of FIGS. 1A-1B in accordance with some embodiments.

FIG. 9A illustrates second exemplary implementation of the system 100 of FIGS. 1A-1B. The catheter 930 may in some respects resemble the catheter 130 of FIGS. 1A, 1B, 5A, 5B, and 7A. As such, the features and functionalities of the catheter 930 may be the same or similar to the features and functionalities of the catheter 130. The implementation of FIG. 9A differs from the implementation of FIG. 7A in that the predetermined subshape pertains to a portion of the optical fiber disposed exterior to the patient. For illustrative purposes, FIG. 9A includes the 3D coordinate axis system 952 having a horizontal x-axis 952A pointing to the right, a vertical y-axis 952B pointing up, and a z-axis 952C pointing into the page to illustrate the 3D space surrounding the patient 700.

As shown in FIG. 9A, a subshape 940 extends along a portion of the catheter 930 disposed external to the patient 700. The shape framing logic 195 may define a reference plane 950 in accordance with the subshape 940 of the 3D shape 935. Similar to the implementation of FIG. 7A, the shape framing logic 195 analyzes the subshape 940 to determine whether the subshape 940 is consistent in shape with a predetermined subshape that may be stored in the data repository 192. Detecting a predetermined shape, may include comparing the subshape 940 with a selected one of a plurality of stored predetermined subshapes in the memory (e.g., the data repository 192) to determine if the subshape 940 is effectively consistent with the selected one of the stored predetermined subshapes. With the subshape 940 determined to be consistent with a predetermined subshape in memory, the subshape 940 may then be defined as the predetermined subshape 941 of the 3D shape 935.

The plurality of stored predetermined subshapes may include a subset of stored predetermined subshapes pertaining to a proximal portion 921 of the catheter 930 external to the patient 700. Selecting a stored predetermined subshape from the plurality of predetermined stored in memory may include receiving input from a clinician. For example, in some embodiments, the catheter 930 may include a guide for defining a pathway for the catheter 930, where the guide defines the subshape 940. In some embodiments, the clinician may form a bend 943 in the catheter 930 along the proximal portion 921 where the bend defines the subshape 940.

The shape framing logic 195 may utilize the segments 945, 946 to define the reference plane 950 via geometric techniques as described above in relation to defining the reference plane 750 of FIG. 7A above.

In some embodiments, the clinician may position/orient the proximal portion 921 in relation to the patient 700. More specifically, the clinician may orient the subshape 940 to be in parallel with the patient 700 so that the reference plane 950 is in parallel with the patient 700.

Figure 9C:
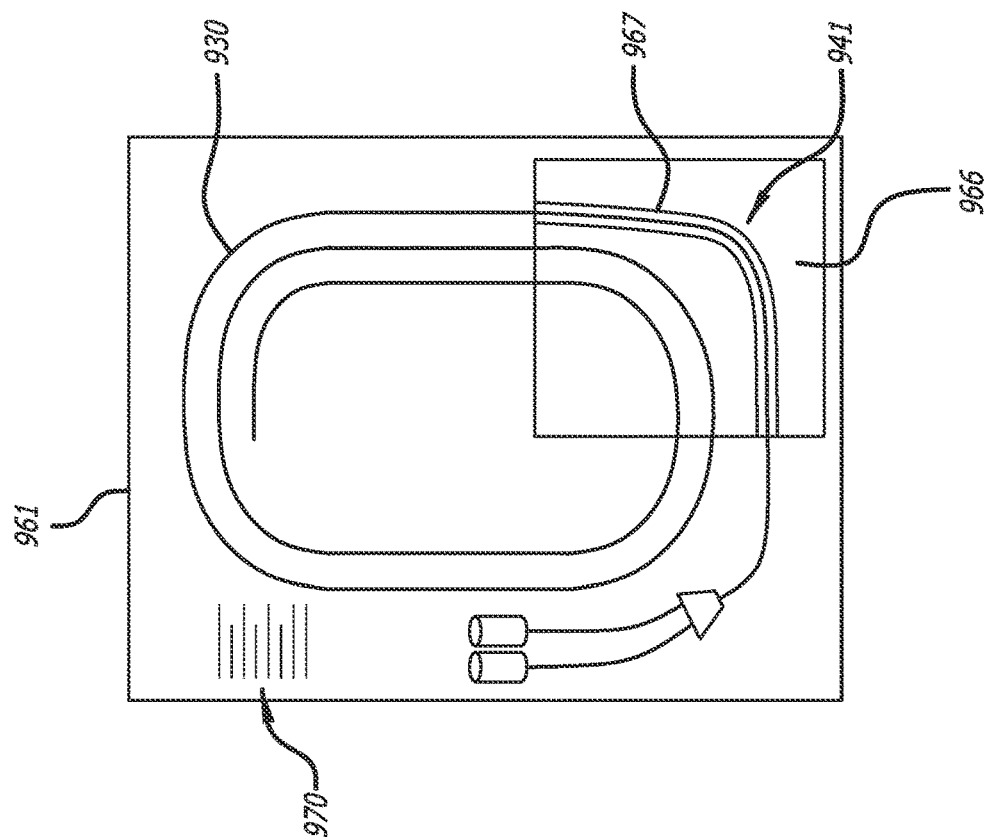
FIGS. 9B-9D illustrate various embodiments of the catheter of FIG. 9A including packaging of the catheter in accordance with some embodiments.
Figure 9B:
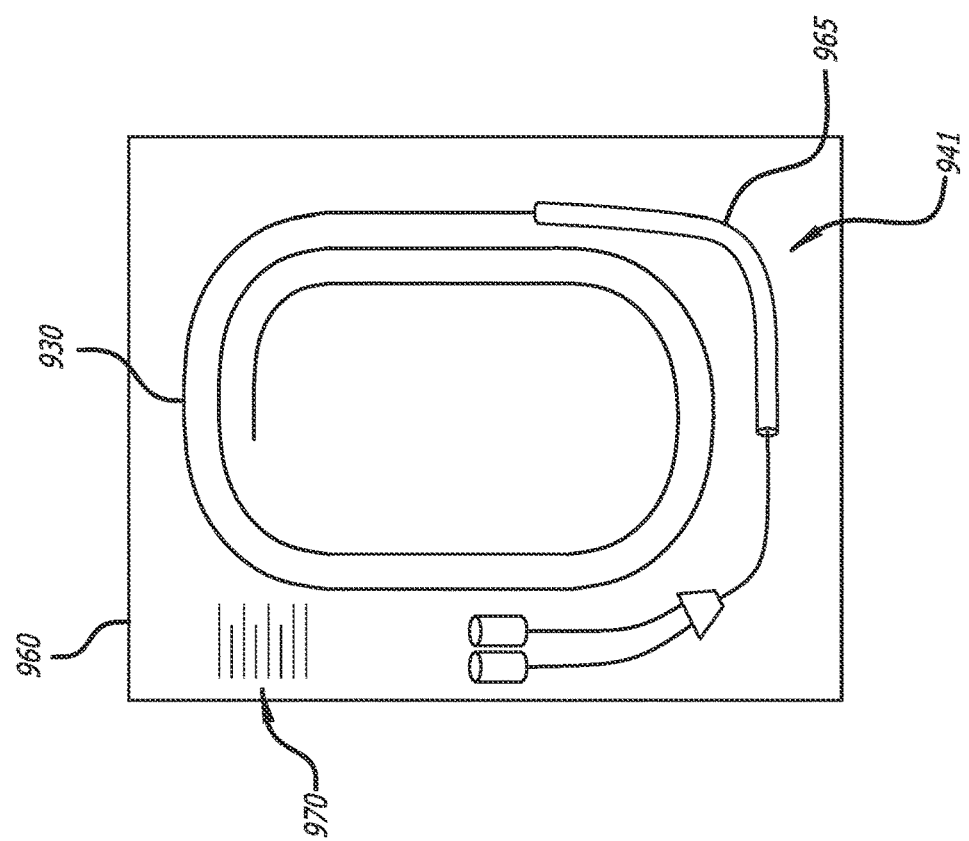

FIG. 9B illustrates a first embodiment of a package 960 containing the catheter 930. The package 960 may be formed of a bag, a pouch, or a hard sided container. The package 960 includes a tubular guide 965 for the catheter 930. The tubular guide 965 is configured to define the predetermined subshape 941. In some embodiments, the catheter 930 is pre-threaded through the tubular guide 965 in a closed state of the package 960 as illustrated. In other embodiments, the catheter 930 may not be pre-threaded through the tubular guide 965, and the clinician may thread the tubular guide 965 onto the catheter 930 after opening the package 960. In some embodiments, the predetermined subshape 941, defined by the tubular guide 965, may be associated with a part number (or other identification information) of the catheter 930, and the shape framing logic 195 may select a stored predetermined shape from memory in accordance with the clinician inputting the part number. In some embodiments, the tubular guide 965 may be integral to the package 960, such as formed in a side wall of the package 960, for example. In some embodiments, the package 960 or a portion thereof may be configured for attachment to the patient so that an orientation of the tubular guide 965 is stable with respect to the patient.

FIG. 9C illustrates a second embodiment of a package 961 containing the catheter 930. The package 961 may be formed of a bag, a pouch, or a hard sided container. The package 961 includes guide plate 966 for the catheter 930. The guide plate 966 includes a groove 967 configured to define the predetermined subshape 941. In some embodiments, the catheter 930 is pre-attached to the guide plate 966 so that catheter 930 is loaded within the groove 967 in a closed state of the package 961 as illustrated. In other embodiments, the catheter 930 may not be pre-loaded within the groove 967, in which case, the clinician may place the catheter 930 within the groove 967 after opening the package 961. In some embodiments, the predetermined subshape 941, defined by the guide plate 966, may be associated with a part number (or other identification information) of the catheter 930, and the shape framing logic 195 may select a stored predetermined shape from memory in accordance with the clinician inputting the part number. In some embodiments, the guide plate 966 may be integral to the package 961, such as formed on a side wall of the package 960, for example. In some embodiments, the guide plate 966 may be separable from the package 961 and may be configured for attachment to the patient so that an orientation of the guide plate 966 is stable with respect to the patient.

Figure 9D:
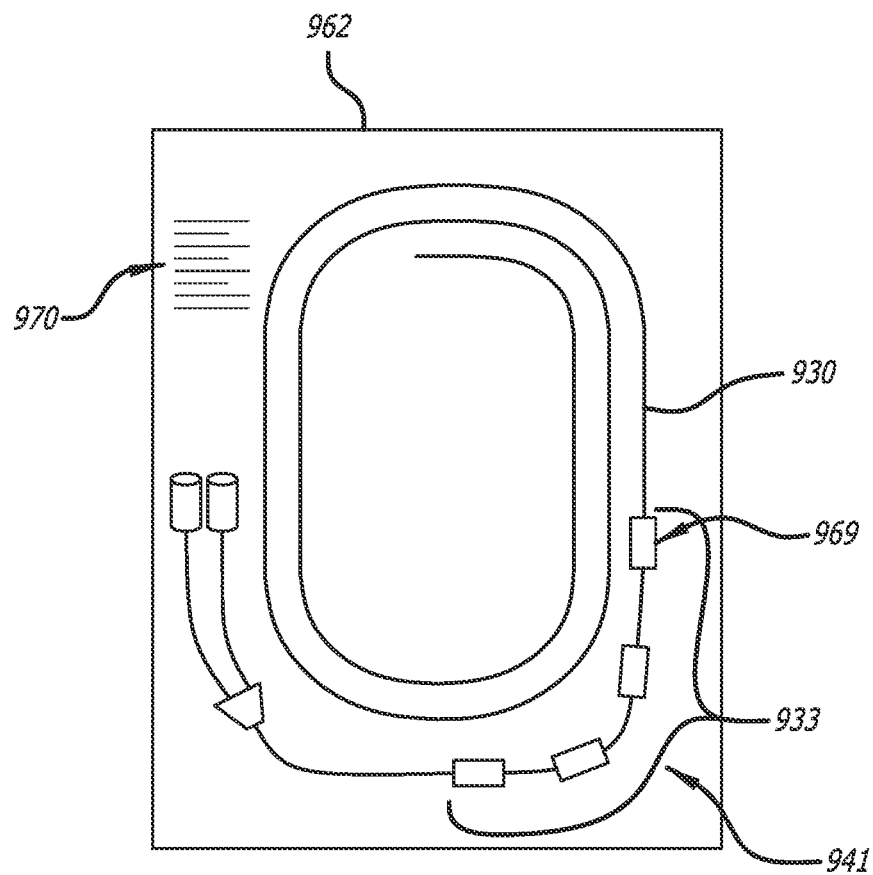

FIG. 9D illustrates a third embodiment of a package 962 containing the catheter 930. The package 962 may be formed of a bag, a pouch, or a hard sided container. In the illustrated embodiment, a portion 933 of the catheter 930 is attached to the package 962 to define the predetermined subshape 941. In some embodiments, the catheter 930 may be continuously attached to a wall of the package 962, or the catheter 930 may be attached at a plurality of the attachment points 969. The attachment mechanism may include an adhesive or structural components (e.g., clips) configured to retain the portion 933 of the catheter 930 at the predetermined subshape 941.

Each of the package embodiments of FIGS. 9B-9D may include package indicia 970. The package indicia 970 may include information relating the predetermined subshape 941. For example, the package indicia 970 may include a part number/model number of the catheter 930 or any other identifying information. The package indicia 970 may include a machine-readable medium such as a bar code, matrix code, RFID, etc. In use, the clinician may input information from the package indicia 970 into the system 100, and the shape framing logic 195 may select a stored predefined shape in memory in accordance with the information from the package indica 970.

Figure 10:
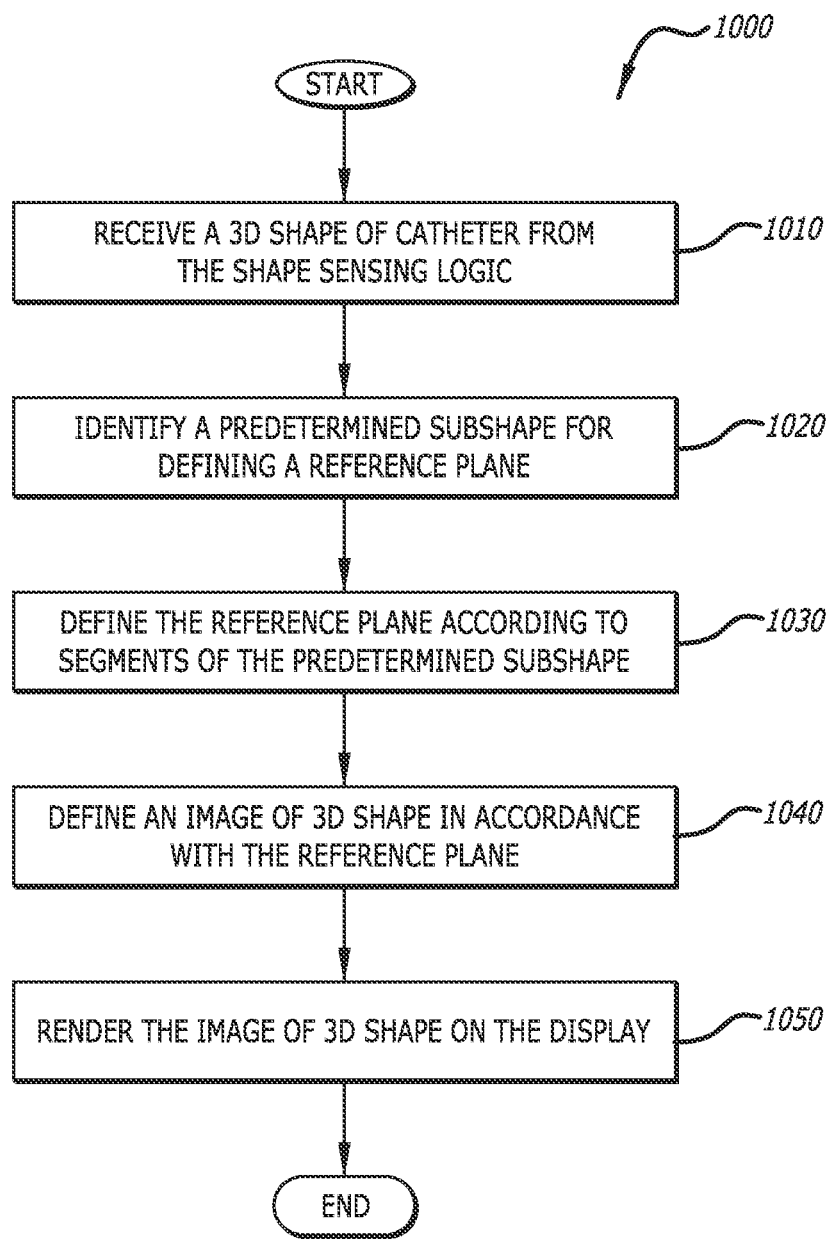
FIG. 10 is a flowchart of a method of operations conducted by the medical instrument monitoring system of FIGS. 1A-1B to display an image of the 3D shape according to the reference plane in accordance with some embodiments.

Referring to FIG. 10, a flowchart of a method of operations conducted by the medical instrument monitoring system of FIGS. 1A-1B to render an image of the 3D shape on the display is shown, in accordance with some embodiments. The method 1000 may be performed by the shape framing logic 195. In some embodiments, portions of the method 1000 may be performed by the shape sensing logic 194. The method 1000 generally processes shape data received from the shape sensing logic 194 to define images of the 3D shapes determined from optical fibers extending along the medical device or portions thereof. According to one embodiment of the disclosure, as shown in FIG. 10, the shape framing logic 195 receives 3D shape data pertaining to the 3D shape of the catheter from the shape sensing logic 194 (block 1010).

The shape framing logic 195 may identify a predetermined subshape disposed along the 3D shape of the medical devise (i.e., the optical fiber extending along the medical device) suitable for defining a reference plane to be used in rendering an image of the 3D shape on the display (block 1020). The 3D shape may generally include one or more subshapes (portions of the 3D shape) that may be suitable for use as the predetermined subshape and the shape framing logic 195 identifies a predetermined subshape from the one or more subshapes. Identifying the predetermined subshape may include comparing the predetermined subshape with a stored predetermined subshape in memory. In an instance where a subshape of the 3D shape matches (i.e., is sufficiently consistent with) a stored predetermined subshape, the shape framing logic 195 may define the subshape as the predetermined subshape for the 3D shape.

The memory may include a plurality of stored predetermined subshapes. The stored predetermined subshapes may be defined in accordance with different pathways for the medical device when the medical device is in use. For example, the medical may be advanced along an anatomical pathway of the patient, such as a predefined vasculature of the patient. As such, a stored predetermined subshape may be consistent with a subshape of the medical device when the medical device is disposed within the predefined vasculature. By way of further example, the medical device may be disposed along a pathway of a guide external to the patient. As such, a stored predetermined subshape may be consistent with a subshape of the medical device when the medical device is disposed within the pathway of the guide.

In some embodiments, the shape framing logic 195 may analyze the shape data of the 3D shape to determine a subshape consistent with at least one of the stored predetermined subshapes and then select one of the stored predetermined subshapes for comparison. In some embodiments, the shape framing logic 195 may receive input from a clinician to assist in determining a subshape consistent with at least one of the stored predetermined subshapes. The input may include information pertaining to a predefined anatomical pathway or a pathway of a guide.

Once a predetermined subshape for the 3D shape is defined, the shape framing logic 195 may then define the reference plane in accordance with the predetermined subshape (block 1030). Defining the reference plane may include identifying shape segments (i.e., portions) of the predetermined subshape. The shape framing logic 195 may define the reference plane utilizing geometric techniques utilizing two or more shape segments, such as lines or points extending along the predetermined subshape. According to one embodiment, the shape framing logic 195 may identify two shape segments which are substantially linear and which not collinear with each other. The shape framing logic 195 may utilize a cross-product geometric technique to define a normal line that is perpendicular to both shape segments and then define the reference plane perpendicular to the normal line. As may be appreciated by one of ordinary skill, other geometric techniques may be utilized to define the plane from the portions of the predetermined subshape.

The shape framing logic 195 may then define an image of the 3D shape in accordance with the reference plane (block 1040). In other words, the shape framing logic 195 may define an image of the 3D shape that may viewed on the display from one or more viewpoints with respect to the reference plane, i.e., from the front, top, right side, etc. In some embodiments, the shape framing logic 195 may define an image of the 3D shape viewable from any direction with respect the reference plane.

The shape framing logic 195 may then render the image of the 3D shape on the display (block 1050). In some embodiments, the shape framing logic 195 may lock the orientation of the reference plane in the 3D space so that movement/reorientation of the 3D shape, as may be caused by movement of the patient 700, may cause a corresponding movement/reorientation of the 3D shape within the image.

In other embodiments, the shape framing logic 195 may lock the reference plane to the predetermined subshape so that the viewing reference of the 3D shape remains constant in the event of patient movement. In still other embodiments, the shape framing logic 195 may continuously define reference plane according to the predetermined subshape during use of the system. In some embodiments, the shape framing logic 195 may selectively lock the reference plane in 3D space or the predetermined subshape 741 in response to input from the clinician.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device system comprising:
a medical device comprising an optical fiber having one or more core fibers, each of the one or more core fibers including a plurality of sensors distributed along a longitudinal length of a corresponding core fiber, each sensor of the plurality of sensors configured to:
   (i) reflect a light signal of a different spectral width based on received incident light, and
   (ii) change a characteristic of the reflected light signal based on strain experienced by the optical fiber; and
a console including one or more processors and a non-transitory computer-readable medium having stored thereon logic, when executed by the one or more processors, causes operations including:
   providing an incident light signal to the optical fiber;
   receiving reflected light signals of different spectral widths of the incident light by one or more of the plurality of sensors;
   processing the reflected light signals associated with the one or more of core fibers to determine a three-dimensional (3D) shape of the optical fiber;
   detecting a predetermined subshape of the 3D shape;
   defining a reference plane in accordance with the predetermined subshape, wherein the reference plane defines a viewing perspective of the 3D shape; and
   orienting the reference plane in 3D space for rendering an image of the 3D shape on a display.

2. The system according to claim 1, wherein detecting the predetermined subshape includes:
   comparing a subshape of the 3D shape with a stored predetermined subshape in memory; and
   as a result of the comparing, identifying the subshape as the predetermined subshape of the 3D shape.

3. The system according to claim 2, wherein:
   the memory includes a plurality of stored predetermined subshapes, and
   the operations further include selecting the stored predetermined subshape from the plurality of stored predetermined subshapes in memory.

4. The system according to claim 1, wherein the predetermined subshape is defined by a predetermined pathway of the medical device.

5. The system according to claim 4, wherein:
   the medical device is configured for insertion within a patient body, and
   the predetermined pathway is defined by an anatomical pathway of the patient body.

6. The system according to claim 5, wherein the operations further include:
   receiving input from a clinician defining the anatomical pathway of the patient body; and
   selecting the stored predetermined subshape according to the input from the clinician.

7. The system according to claim 6, wherein the input from the clinician includes a location of an insertion site for the medical device.

8. The system according to claim 7, wherein in use, the clinician inserts the medical device within a pathway of a subshape guide.

9. The system according to claim 5, wherein the anatomical pathway extends along one or more of a basilic vein, a subclavian vein, an innominate vein, an internal jugular vein, an external jugular vein, or a superior vena cava of the patient body.

10. The system according to claim 4, wherein the predetermined pathway is external to a patient.

11. The system according to claim 10, wherein:
    the predetermined pathway is defined by a subshape guide of the medical device, and
    in use, the medical device is disposed within a pathway of the subshape guide.

12. The system according to claim 11, wherein the subshape guide is included within a package of the medical device.

13. The system according to claim 12, wherein the subshape guide is formed integral to the package.

14. The system according to claim 11, wherein in use, the subshape guide is attached to a patient to maintain an orientation of the predetermined subshape with respect to the patient.

15. The system according to claim 1, wherein defining the reference plane includes:
    identifying a pair of shape segments of the predetermined subshape, and
    defining a plane in parallel with both shape segments.

16. The system according to claim 1, further comprising:
    a device guide including a lumen extending along a straight section of the device guide, wherein:
    in use, the medical device is inserted within the lumen, and
    the operations further include:
       interpreting a section of the optical fiber disposed within the straight section as a straight line; and
       calibrating the optical fiber in accordance with the straight section.

17. The system according to claim 1, wherein the medical device is selected from the group consisting of an introducer wire, a guidewire, a stylet, a stylet within a needle, a needle with the optical fiber inlayed into a cannula of the needle, and a catheter with the optical fiber inlayed into one or more walls of the catheter.

18. The system according to claim 1, wherein the operations further include rendering the image of the 3D shape on the display of the system in accordance with the reference plane.

19. A method for detecting placement of a medical device within a patient body, the method comprising:
    providing by a system, an incident light signal to an optical fiber included within the medical device, wherein the optical fiber includes one or more core fibers, each of the one or more core fibers including a plurality of reflective gratings distributed along a longitudinal length of a corresponding core fiber and each of the plurality of reflective gratings being configured to (i) reflect a light signal of a different spectral width based on received incident light, and (ii) change a characteristic of the reflected light signal based on strain experienced by the optical fiber;
    receiving reflected light signals of different spectral widths of the incident light signal by one or more of a plurality of sensors;
    processing the reflected light signals associated with the one or more core fibers to determine a three-dimensional (3D) shape of the optical fiber;
    detecting a predetermined subshape of the 3D shape;
    defining a reference plane in accordance with the predetermined subshape, wherein the reference plane defines a viewing perspective of the 3D shape; and
    orienting the reference plane in 3D space for rendering an image of the 3D shape on a display.

20. The method according to claim 19, wherein detecting the predetermined subshape includes:
  comparing a subshape of the 3D shape with a stored predetermined subshape in memory of the system; and
  as a result of the comparing, identifying the subshape as the predetermined subshape of the 3D shape.

21. The method according to claim 20, further comprising selecting the stored predetermined subshape from a plurality of stored predetermined subshapes in memory.

22. The method according to claim 19, wherein the predetermined subshape is defined by a predetermined pathway of the medical device.

23. The method according to claim 22, wherein the predetermined pathway is defined by an anatomical pathway of the patient body.

24. The method according to claim 20, further comprising:
  receiving input from a clinician defining the anatomical pathway of the patient body; and
  selecting the stored predetermined subshape according to the input from the clinician.

25. The method according to claim 24, wherein the input from the clinician includes a location of an insertion site for the medical device.

26. The method according to claim 23, wherein the anatomical pathway extends along one or more of a basilic vein, a subclavian vein, an innominate vein, an internal jugular vein, an external jugular vein, or a superior vena cava of the patient body.

27. The method according to claim 23, wherein the predetermined pathway is external to the patient body.

28. The method according to claim 19, further comprising:
  identifying a pair of shape segments of the predetermined subshape, and
  defining a plane in parallel with both shape segments.

29. The method according to claim 19, wherein in use, the medical device is inserted within a lumen of a medical device guide of the system, the method further comprising calibrating the optical fiber in accordance with a straight section of the medical device guide.

30. The method according to claim 19, wherein the medical device is selected from the group consisting of an introducer wire, a guidewire, a stylet, a stylet within a needle, a needle with the optical fiber inlayed into a cannula of the needle, and a catheter with the optical fiber inlayed into one or more walls of the catheter.

31. The method according to claim 19, further comprising rendering the image of the 3D shape on the display of the system in accordance with the reference plane.

* * * * *